United States Patent
Dealwis et al.

(10) Patent No.: US 11,439,623 B2
(45) Date of Patent: Sep. 13, 2022

(54) METHOD OF MODULATING RIBONUCLEOTIDE REDUCTASE

(71) Applicant: CASE WESTERN RESERVE UNIVERSITY, Cleveland, OH (US)

(72) Inventors: Chris G. Dealwis, Cleveland, OH (US); Rajesh Viswanathan, Cleveland, OH (US); Sarah E. Huff, Cleveland, OH (US); William Harte, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 105 days.

(21) Appl. No.: 16/500,700

(22) PCT Filed: Apr. 4, 2018

(86) PCT No.: PCT/US2018/026098
§ 371 (c)(1),
(2) Date: Oct. 3, 2019

(87) PCT Pub. No.: WO2018/187479
PCT Pub. Date: Oct. 11, 2018

(65) Prior Publication Data
US 2021/0113533 A1  Apr. 22, 2021

Related U.S. Application Data

(60) Provisional application No. 62/481,458, filed on Apr. 4, 2017.

(51) Int. Cl.
*A61K 31/4245* (2006.01)
*A61K 31/4439* (2006.01)
*A61K 45/06* (2006.01)

(52) U.S. Cl.
CPC ...... *A61K 31/4245* (2013.01); *A61K 31/4439* (2013.01); *A61K 45/06* (2013.01)

(58) Field of Classification Search
CPC ............ A61K 31/4192; A61K 31/4196; A61K 31/4245; A61K 31/4439; A61K 45/06; A61P 35/00; C07C 251/86
See application file for complete search history.

(56) References Cited

U.S. PATENT DOCUMENTS

| | | | |
|---|---|---|---|
| 7,317,029 B2 | 1/2008 | Cai et al. | |
| 7,799,811 B2 | 9/2010 | Kwon et al. | |
| 8,440,698 B2 | 5/2013 | Takeuchi et al. | |
| 8,492,378 B2 | 7/2013 | Itoh et al. | |
| 8,796,320 B2 | 8/2014 | Asai et al. | |
| 8,802,704 B2 | 8/2014 | Quattropani et al. | |
| 10,071,081 B2 | 9/2018 | Karp et al. | |
| 10,155,753 B2 | 12/2018 | Byun et al. | |
| 10,183,082 B2 | 1/2019 | Tian et al. | |
| 10,478,430 B2 | 11/2019 | Pollard et al. | |
| 10,479,784 B2 | 11/2019 | Charrier et al. | |
| 10,653,677 B2 | 5/2020 | Combs et al. | |
| 2001/0039291 A1 | 11/2001 | Camden | |
| 2005/0004005 A1 | 1/2005 | Kasibhatla et al. | |
| 2006/0052317 A1 | 3/2006 | Lori et al. | |
| 2007/0004642 A1 | 1/2007 | Ohmoto et al. | |
| 2008/0139632 A1* | 6/2008 | Almstead | A61P 25/00 514/364 |
| 2008/0255203 A1 | 10/2008 | Lee et al. | |
| 2009/0176742 A1 | 7/2009 | Henderson et al. | |
| 2011/0207704 A1 | 8/2011 | Cusack et al. | |
| 2011/0311485 A1 | 12/2011 | Giulio Matassa et al. | |
| 2015/0094314 A1 | 4/2015 | Dealwis | |
| 2019/0185462 A1 | 6/2019 | Walji et al. | |

FOREIGN PATENT DOCUMENTS

| | | | | |
|---|---|---|---|---|
| WO | WO-2006044682 A1 * | 4/2006 | | A61P 9/00 |
| WO | 2019/106579 A1 | 6/2019 | | |

OTHER PUBLICATIONS

Rapolu et al. (European Journal of Medicinal Chemistry (2013), vol. 66, pp. 91-100) (Year: 2013).*
Khan et al., Med. Chem. Res, publ. 2013., vol. 22, pp. 6022-6028 (Year: 2013).*
Rodriguez, "Know the most common types of cancer", Everyday Health, publ. Feb. 8, 2010, pp. 1-13 (Year: 2010).*
Mandal, "How to prevent cancer", http://www.news-medical.net/health/How-to-Prevent-Cancer.aspx, publ. Aug. 29, 2013, pp. 1-4 (Year: 2013).*
Fontebasso et al., Crit. Rev. Oncog., publ. 2015, vol. 20(5-6), pp. 1-33 (Year: 2015).*
Alexander, MD Anderson Cancer Center, "Can you prevent cancer?", publ. Jan. 2020, pp. 1-3 (Year: 2020).*
Brockman et al., "Inhibition of Ribonucleotide Reductase, DNA Synthesis, and L1210 Leukemia by Guanazole", Cancer Research, Sep. 1970, vol. 30, pp. 2358-2368; Title, p. 2358, p. 2359.
European Article 94(3) EPC dated Sep. 4, 2020.

* cited by examiner

*Primary Examiner* — Sarah Pihonak
(74) *Attorney, Agent, or Firm* — Tarolli, Sundheim, Covell & Tummino LLP

(57) ABSTRACT

A method of modulating ribonucleotide reductase activity in a neoplastic cell includes administering to the cell an amount of a triazole or an oxadiazole ribonucleotide reductase modulator (RRmod), the amount being effective to inhibit neoplastic cell growth.

12 Claims, 2 Drawing Sheets

METHOD OF MODULATING RIBONUCLEOTIDE REDUCTASE

RELATED APPLICATION

This application claims priority from U.S. Provisional Application No. 62/481,458, filed Apr. 4, 2017, the subject matter of which is incorporated herein by reference in its entirety.

GOVERNMENT FUNDING

This invention was made with government support under Grant No. R01GM100887 and R01CA100827 awarded by The National Institutes of Health. The United States government has certain rights in the invention.

FIELD OF THE INVENTION

The present invention relates to modulators of ribonucleotide reductase (RR) and to methods of using such modulators for therapeutic applications.

BACKGROUND

Ribonucleotide reductase (RR) is a highly regulated enzyme which catalyzes the de novo dNTP synthesis pathway that is ubiquitously present in human, bacteria, yeast, and other organisms. RR plays a crucial role in de novo DNA synthesis by reducing ribonucleoside diphosphates to 2'-deoxy ribonucleoside diphosphates and maintains balanced pools of deoxynucleoside triphosphates (dNTPs) in the cell.

RRs are divided into three classes, I to III, based on the method of free-radical generation. All eukaryotic organisms encode a class I RR, consisting of an αnβn multi-subunit protein complex, in which the minimally active form is α2β2. The α or RR1 (large) subunit contains the catalytic (C-site) and two allosteric sites, while the β or RR2 subunit houses a stable tyrosyl free radical that is transferred some 35 Å to the catalytic site to initiate radical-based chemistry on the substrate.

RR is regulated transcriptionally, allosterically and, in the yeast *S. cerevisiae*, RR is further regulated by subunit localization and by its protein inhibitor Sml1. In mammalian cells, RR activity is also controlled by the RR2 levels. Consistent with the varying RR2 levels, dNTP pools also vary with the phases of the cell cycle, reaching the highest concentration during S-phase. RR is regulated by an intricate allosteric mechanism. The two previously described allosteric sites of RR are the specificity site (S-site), which determines substrate preference, and the activity site (A-site), which stimulates or inhibits RR activity depending on whether ATP or dATP is bound.

RR is directly involved in neoplastic tumor growth, metastasis, and drug resistance. The proliferation of cancer cells requires excess dNTPs for DNA synthesis. Therefore, an increase in RR activity is necessary as it helps provide extra dNTPs for DNA replication in primary and metastatic cancer cells. Because of this critical role in DNA synthesis, RR represents an important target for cancer therapy. However, existing chemotherapies that target ribonucleotide reductase are nucleoside-based analogs. Hence, they are promiscuous, leading to nonspecific binding of other nucleoside binding proteins, which results in unwanted side effects.

SUMMARY

Embodiments described herein relate to compounds and methods of modulating ribonucleotide reductase activity in a neoplastic cell. In some embodiments, the method can include administering to a neoplastic cell an amount of a ribonucleotide reductase modulator (RRmod) effective to inhibit neoplastic cell growth.

In some embodiments, the RRmod can be a triazole or analog thereof. The triazole can include a compound having the formula (I):

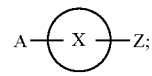

(I)

wherein X is a triazole;

A and Z are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, piperidine, pyridine, pyrazine, pyrimidine, pyridazine, groups incorporating amino acids or other moieties expected to bear positive or negative charge at physiological pH; and pharmaceutically acceptable salts thereof.

In some embodiments, X is selected from the group consisting of:

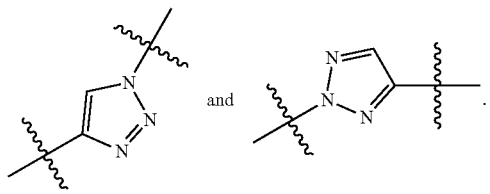 [SMILES: *c1cn(*)nn1 ; *c1cnn(*)n1]

In some embodiments, A and Z are independently selected from the group consisting of:

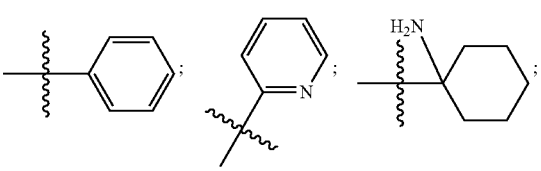

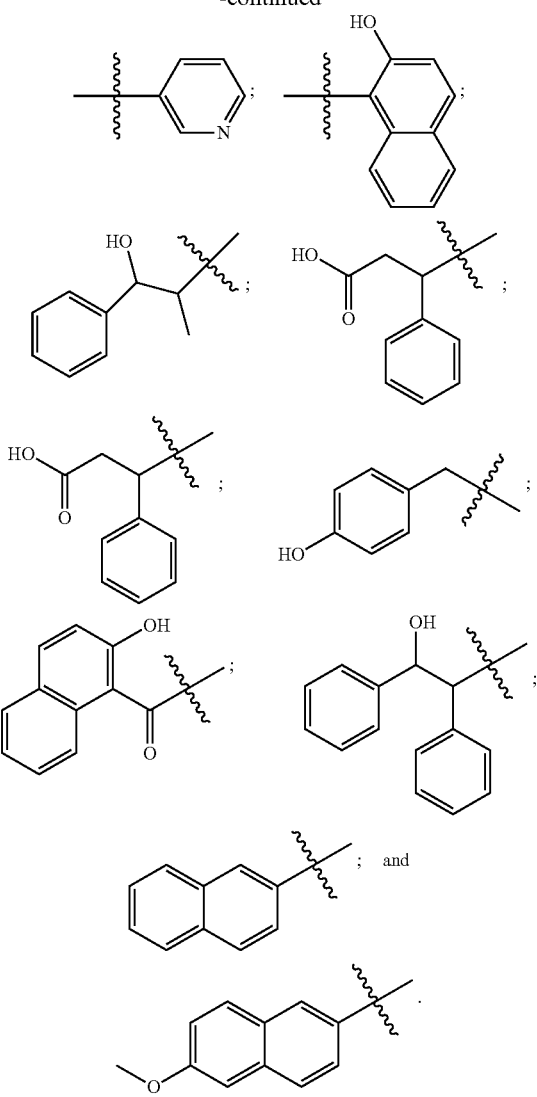
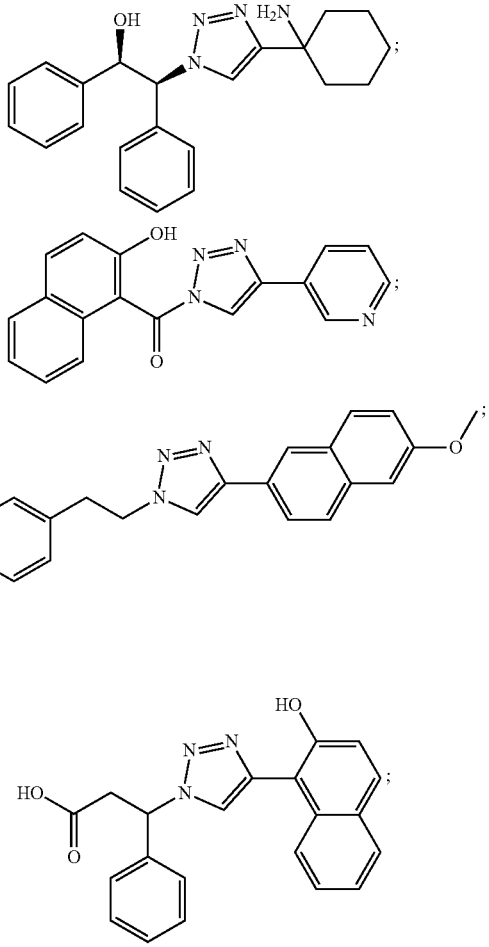
In certain embodiments, an RRmod having formula (I) can be selected from the group consisting of:
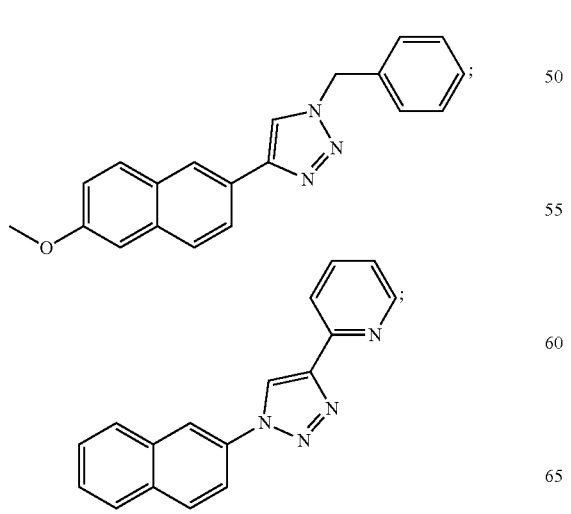
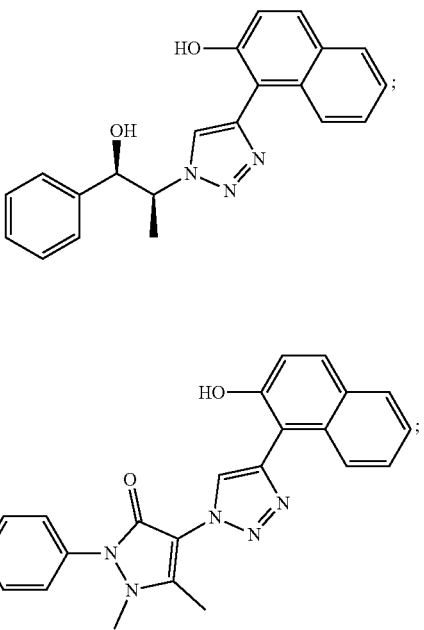
and pharmaceutically acceptable salts thereof.

In some embodiments the RRmod can be an oxadiazole or analog thereof. The oxadiazole can include a compound having the formula (II):

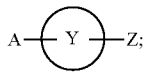
(II)

wherein Y is an oxadiazole;

A and Z are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, piperidine, pyridine, pyrazine, pyrimidine, pyridazine, groups incorporating amino acids or other moieties expected to bear positive or negative charge at physiological pH; and pharmaceutically acceptable salts thereof.

In some embodiments, Y is selected from the group consisting of:

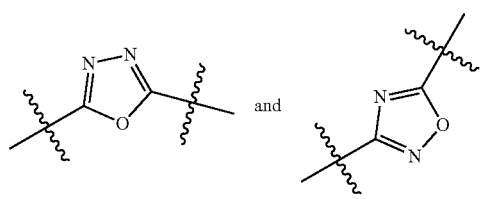

In some embodiments the RRmod can be an oxadiazole compound having the formula (III):

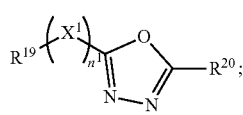
(III)

wherein $X^1$ is $CH_2$, COH, C=O, $CH_2$C=O, or $CH_2$CH($NH_2$);

$n^1$ is 0 or 1;

$R^{19}$ and $R^{20}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, pyridine, groups incorporating amino acids or other moieties expected to bear positive or negative charge at physiological pH; and pharmaceutically acceptable salts thereof.

In other embodiments, the RRmod is an oxadiazole having the following formula (IV):

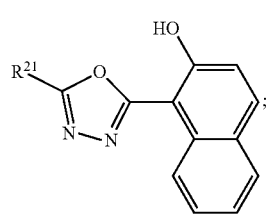
(IV)

wherein $R^{21}$ can be selected from the group consisting of:

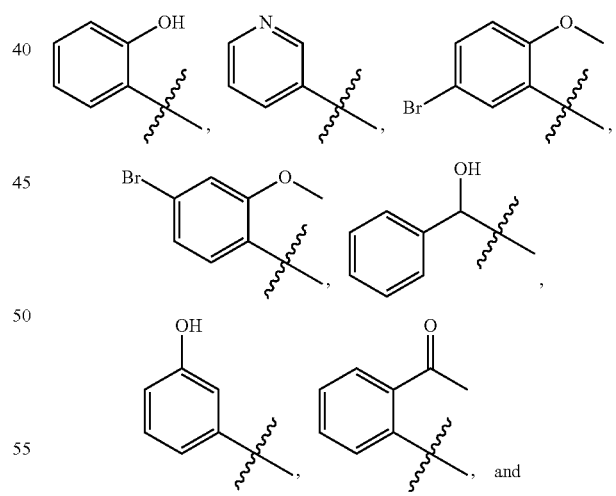

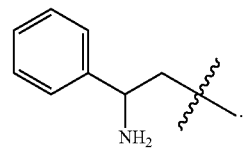

In certain embodiments, an RRmod having formula (III) can be selected from the group consisting of:

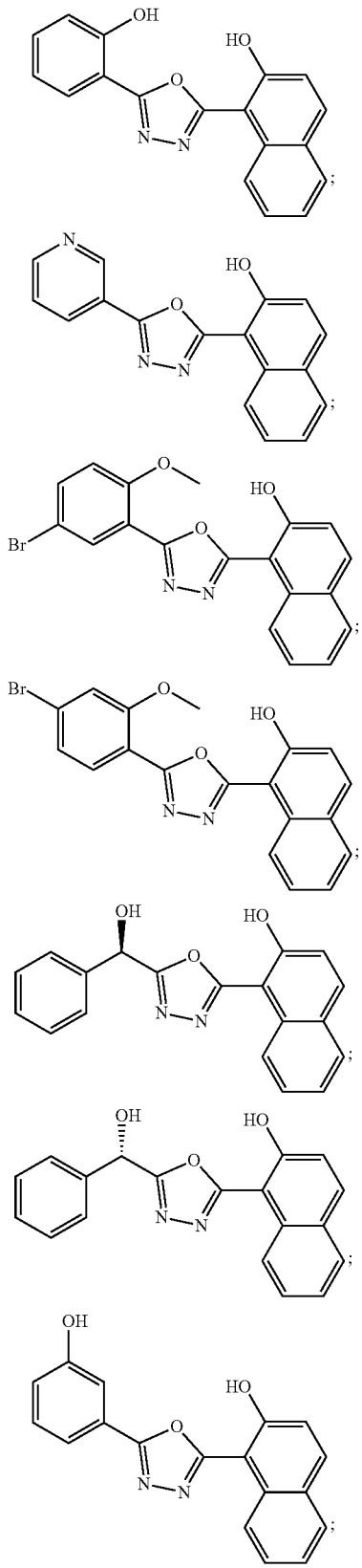

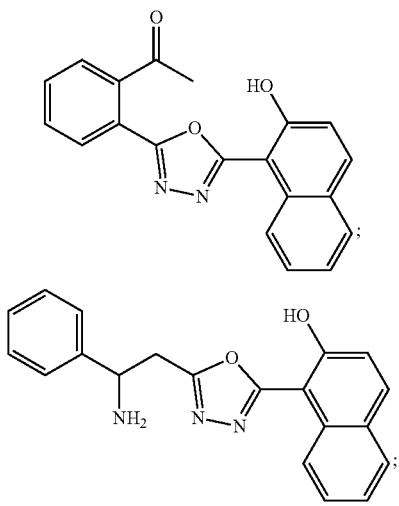

and pharmaceutically acceptable salts thereof.

In other embodiments, the RRmod is an oxadiazole having the following formula (V):

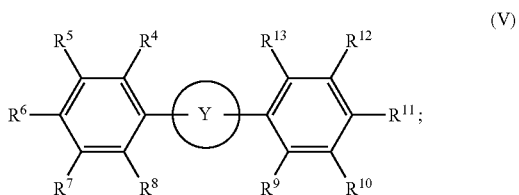

wherein Y is an oxadiazole;

$R^4$ to $R^{13}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, pyridine, groups incorporating amino acids or other moieties expected to bear positive or negative charge at physiological pH; and pharmaceutically acceptable salts thereof, wherein adjacent R groups can be linked to form a cyclic or polycyclic ring, wherein the ring is a substituted or unsubstituted aryl, heteroaryl, cycloalkyl or heterocyclyl.

In other embodiments, the RRmod is an oxadiazole having the following formula (VI):

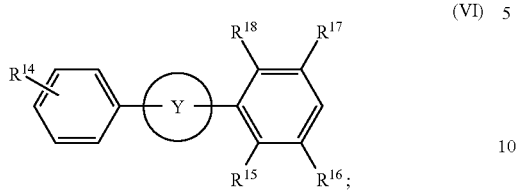

wherein Y is an oxadiazole;
$R^{14}$ is H, OH or a halogen; and
$R^1$ to $R^{18}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, pyridine, groups incorporating amino acids or other moieties expected to bear positive or negative charge at physiological pH; and pharmaceutically acceptable salts thereof, wherein $R^{15}$ and $R^{16}$ or $R^{17}$ and $R^{18}$ can be linked to form a cyclic or polycyclic ring, wherein the ring is a substituted or unsubstituted aryl, heteroaryl, cycloalkyl or heterocyclyl.

Other embodiments relate to a method of treating a neoplastic disorder. The method includes administering to neoplastic cells of the subject a therapeutically effective amount of a pharmaceutical composition. The pharmaceutical composition includes an RRmod. The therapeutically effective amount of an RRmod is an amount effective to inhibit neoplastic cell growth in the subject.

In some embodiments, the RRmod can be a triazole or analog thereof. The triazole can include a compound having the formula (I):

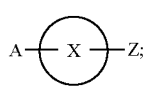

wherein X is a triazole;
A and Z are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, piperidine, pyridine, pyrazine, pyrimidine, pyridazine, groups incorporating amino acids or other moieties expected to bear positive or negative charge at physiological pH; and pharmaceutically acceptable salts thereof.

In some embodiments, X is selected from the group consisting of:

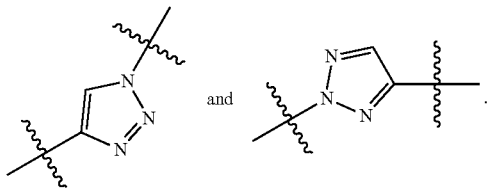

In some embodiments, A and Z are independently selected from the group consisting of:

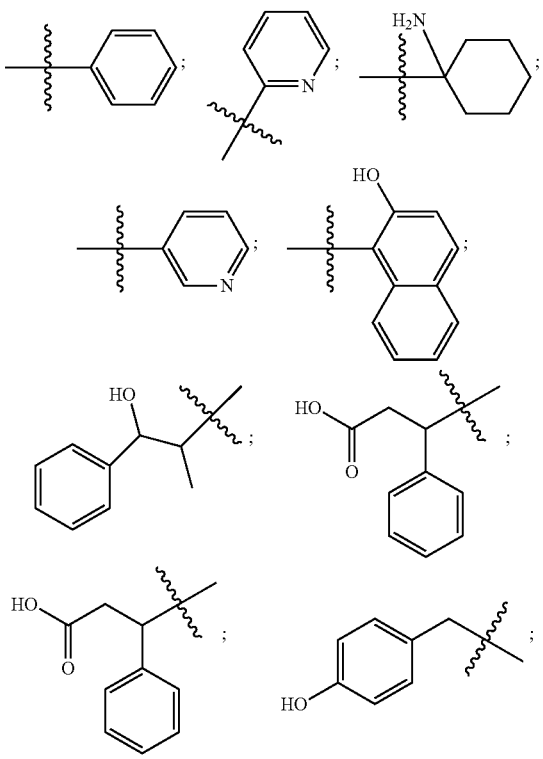

-continued

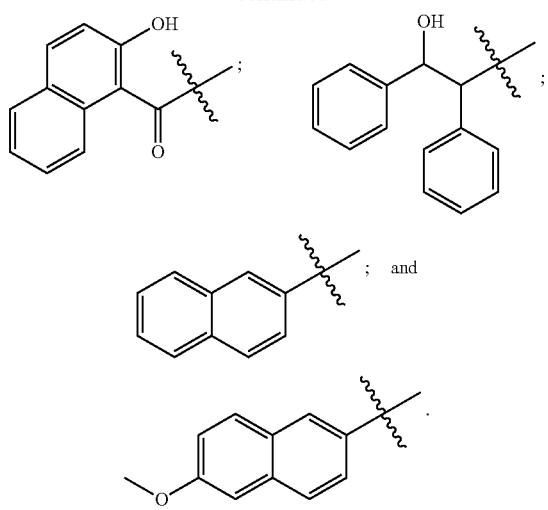

In certain embodiments, an RRmod having formula (I) can be selected from the group consisting of:

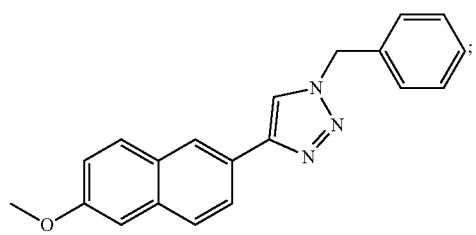

-continued

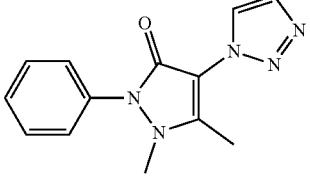
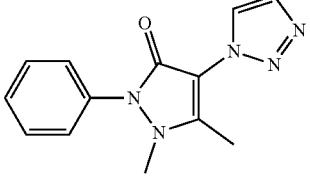

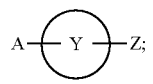

and pharmaceutically acceptable salts thereof.

In some embodiments the RRmod can be an oxadiazole or analog thereof. The oxadiazole can include a compound having the formula (II):

$$A-Y-Z; \quad (II)$$

wherein Y is an oxadiazole;
A and Z are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, piperidine, pyridine, pyrazine, pyrimidine, pyridazine, groups

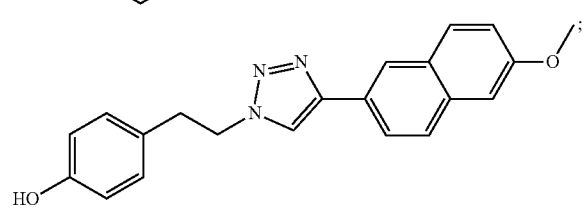

incorporating amino acids or other moieties expected to bear positive or negative charge at physiological pH; and pharmaceutically acceptable salts thereof.

In some embodiments, Y is selected from the group consisting of:

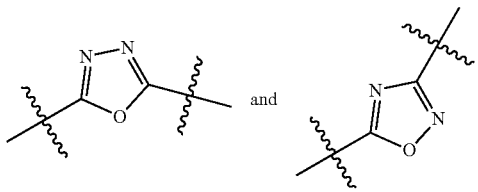

and

In some embodiments the RRmod can be an oxadiazole compound having the formula (III):

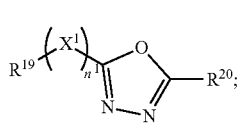

(III)

wherein X is $CH_2$, COH, C=O, $CH_2C$=O, or $CH_2CH(NH_2)$;

$n^1$ is 0 or 1;

$R^{19}$ and $R^{20}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, pyridine, groups incorporating amino acids or other moieties expected to bear positive or negative charge at physiological pH; and pharmaceutically acceptable salts thereof.

In other embodiments, the RRmod is an oxadiazole having the following formula (IV):

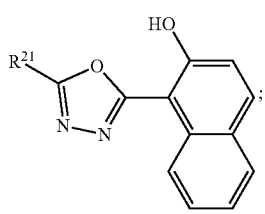

(IV)

wherein $R^{21}$ is selected from the group consisting of:

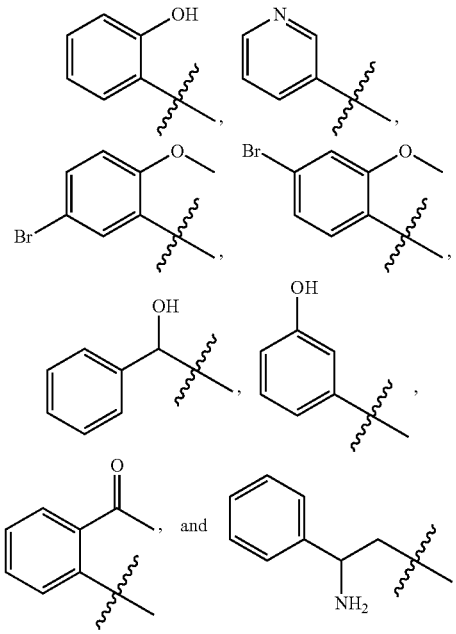

In certain embodiments, an RRmod having formula (III) can be selected from the group consisting of:

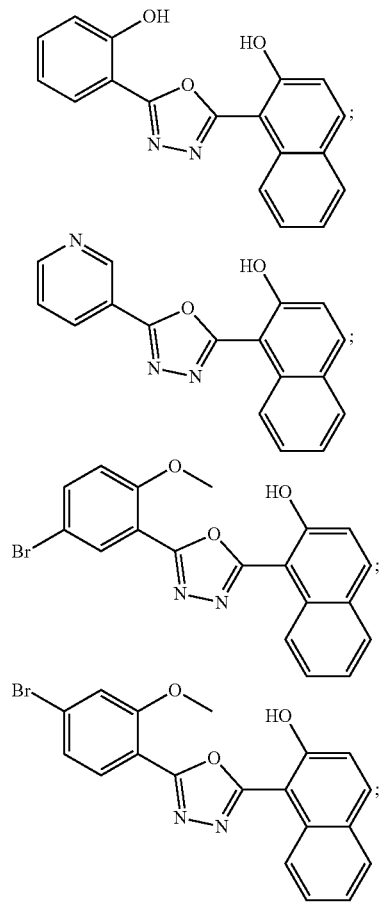

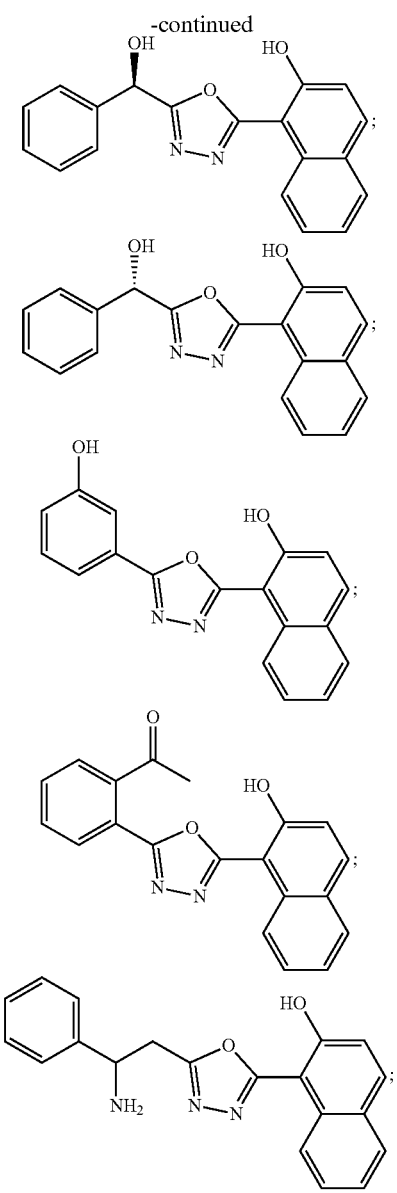

and pharmaceutically acceptable salts thereof.

In other embodiments, the RRmod is an oxadiazole having the following formula (V):

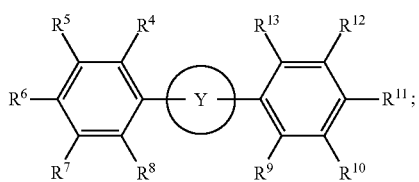

wherein Y is an oxadiazole;

$R^4$ to $R^{13}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, pyridine, groups incorporating amino acids or other moieties expected to bear positive or negative charge at physiological pH; and pharmaceutically acceptable salts thereof, wherein adjacent R groups can be linked to form a cyclic or polycyclic ring, wherein the ring is a substituted or unsubstituted aryl, heteroaryl, cycloalkyl or heterocyclyl.

In other embodiments, the RRmod is an oxadiazole having the following formula (VI):

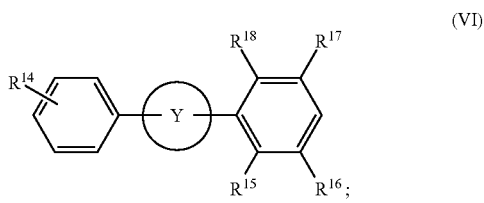

wherein Y is an oxadiazole;

$R^{14}$ is H, OH or a halogen; and $R^{15}$ to $R^{18}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, pyridine, groups incorporating amino acids or other moieties expected to bear positive or negative charge at physiological pH; and pharmaceutically acceptable salts thereof, wherein $R^{15}$ and $R^{16}$ or $R^{17}$ and $R^{18}$ can be linked to form a cyclic or polycyclic ring, wherein the ring is a substituted or unsubstituted aryl, heteroaryl, cycloalkyl or heterocyclyl.

Still other embodiments relate to a pharmaceutical composition that includes an RRmod. The RRmod inhibits cell growth when administered to a neoplastic cell. In some embodiments the RRmod can include a triazole having the formula (I):

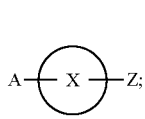
(I)

wherein X is a triazole;
A and Z are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, piperidine, pyridine, pyrazine, pyrimidine, pyridazine, groups incorporating amino acids or other moieties expected to bear positive or negative charge at physiological pH; and pharmaceutically acceptable salts thereof.

In some embodiments, X is selected from the group consisting of:

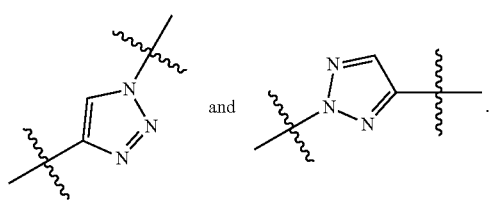 [SMILES: *c1cn(*)nn1 ; *c1cnn(*)n1]

In some embodiments, A and Z are independently selected from the group consisting of:

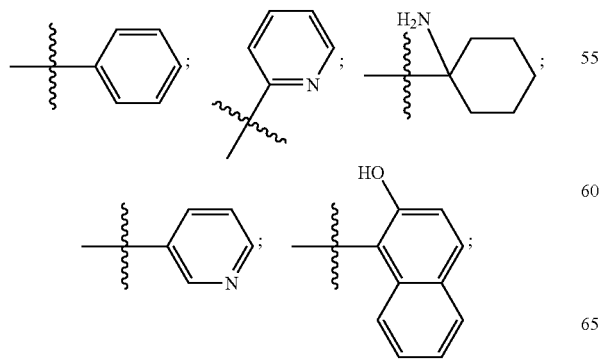

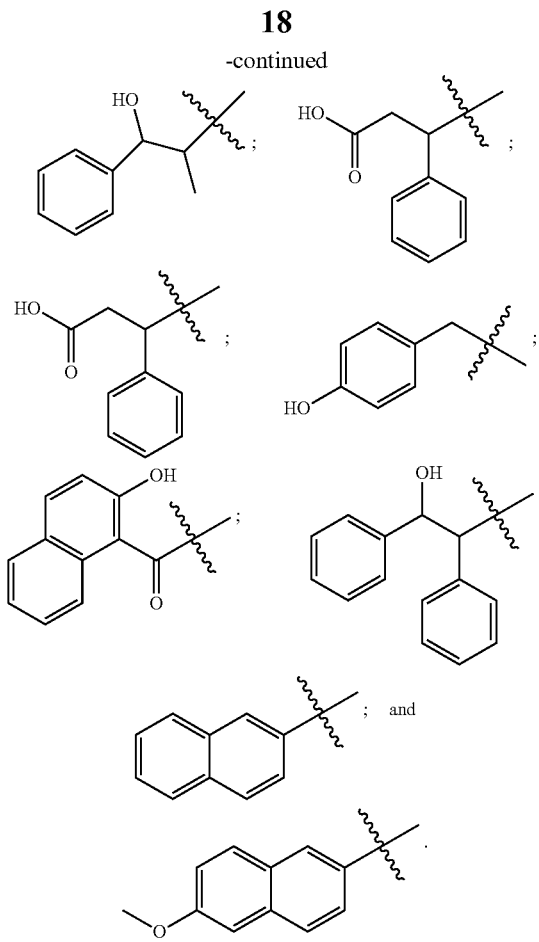

In certain embodiments, an RRmod having formula (I) can be selected from the group consisting of:

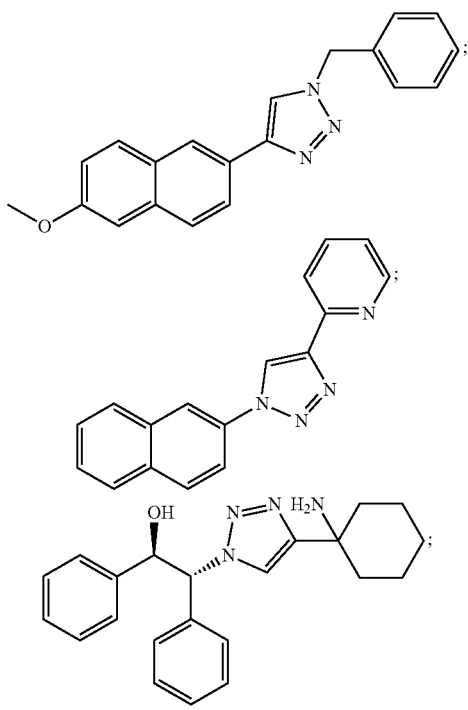

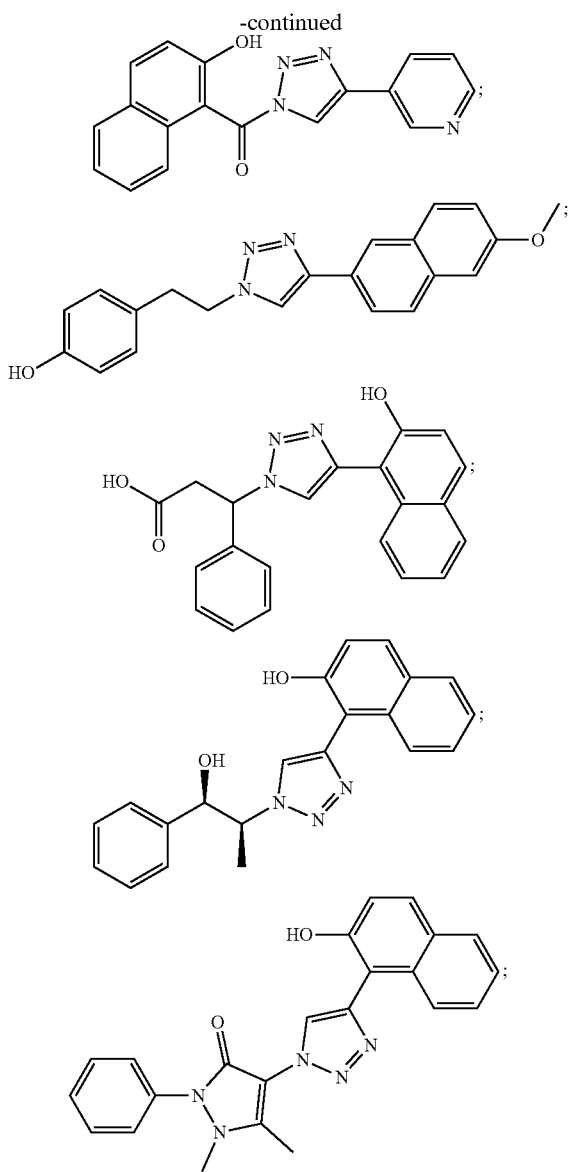

and pharmaceutically acceptable salts thereof.

Further embodiments relate to a pharmaceutical composition that comprises a RRmod including an oxadiazole or analog thereof. The oxadiazole can include a compound having the formula (II):

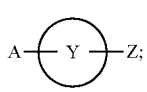

(II)

wherein Y is an oxadiazole;
A and Z are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, piperidine, pyridine, pyrazine, pyrimidine, pyridazine, groups incorporating amino acids or other moieties expected to bear positive or negative charge at physiological pH; and pharmaceutically acceptable salts thereof.

In some embodiments, Y is selected from the group consisting of:

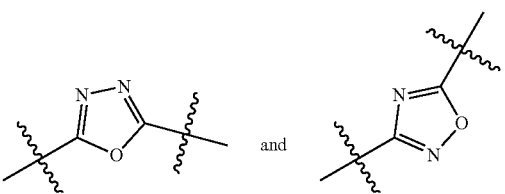

and

In some embodiments the RRmod can be an oxadiazole compound having the formula (III):

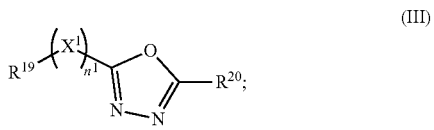

(III)

wherein $X^1$ is $CH_2$, COH, C=O, $CH_2$C=O, or $CH_2$CH($NH_2$);
$n^1$ is 0 or 1;
$R^{19}$ and $R^{20}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, pyridine, groups incorporating amino acids or other moieties expected to bear positive or negative charge at physiological pH; and pharmaceutically acceptable salts thereof.

In other embodiments, the RRmod is an oxadiazole having the following formula (IV):
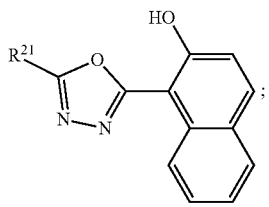
(IV)
wherein R²¹ is selected from the group consisting of:
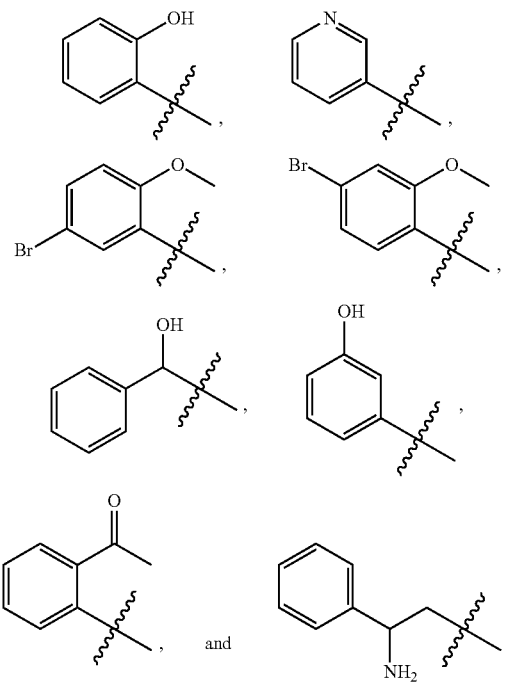
In certain embodiments, an RRmod having formula (III) can be selected from the group consisting of:
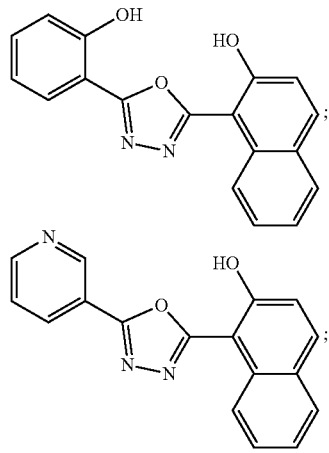
-continued
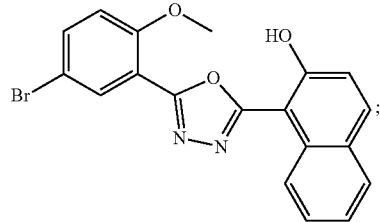
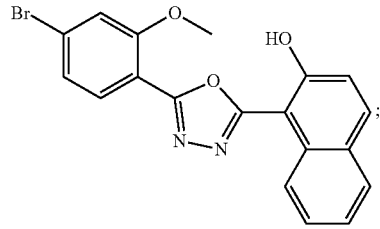
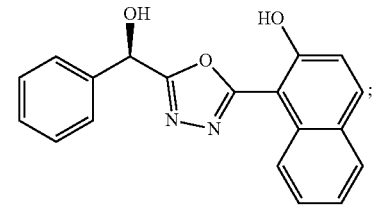
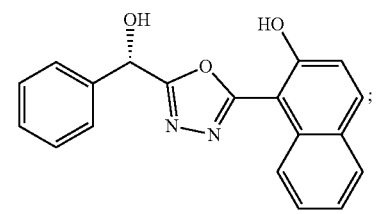
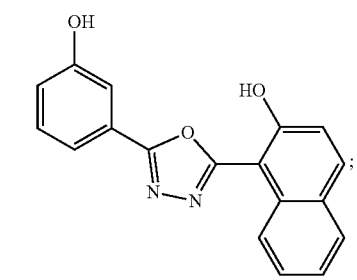
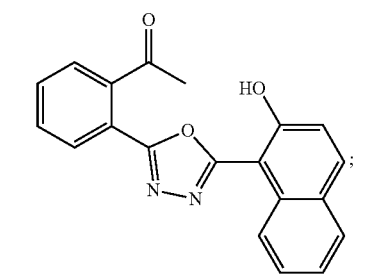
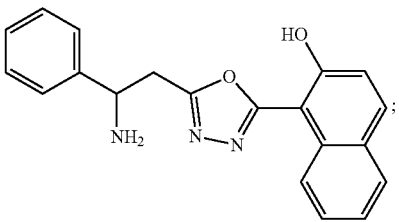
and pharmaceutically acceptable salts thereof.

In other embodiments, the RRmod is an oxadiazole having the following formula (V):

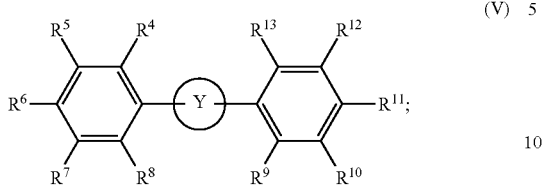

(V)

wherein Y is an oxadiazole;
$R^4$ to $R^{13}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, pyridine, groups incorporating amino acids or other moieties expected to bear positive or negative charge at physiological pH; and pharmaceutically acceptable salts thereof, wherein adjacent R groups can be linked to form a cyclic or polycyclic ring, wherein the ring is a substituted or unsubstituted aryl, heteroaryl, cycloalkyl or heterocyclyl.

In other embodiments, the RRmod is an oxadiazole having the following formula (VI):

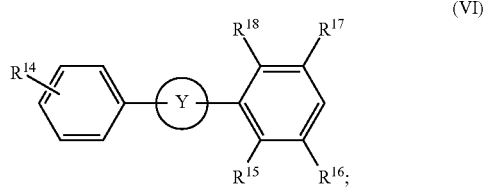

(VI)

wherein Y is an oxadiazole;
$R^{14}$ is H, OH or a halogen; and
$R^{15}$ to $R^{18}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, pyridine, groups incorporating amino acids or other moieties expected to bear positive or negative charge at physiological pH; and pharmaceutically acceptable salts thereof, wherein $R^{15}$ and $R^{16}$ or $R^{17}$ and $R^{18}$ can be linked to form a cyclic or polycyclic ring, wherein the ring is a substituted or unsubstituted aryl, heteroaryl, cycloalkyl or heterocyclyl.

DETAILED DESCRIPTION

Figure 1A:
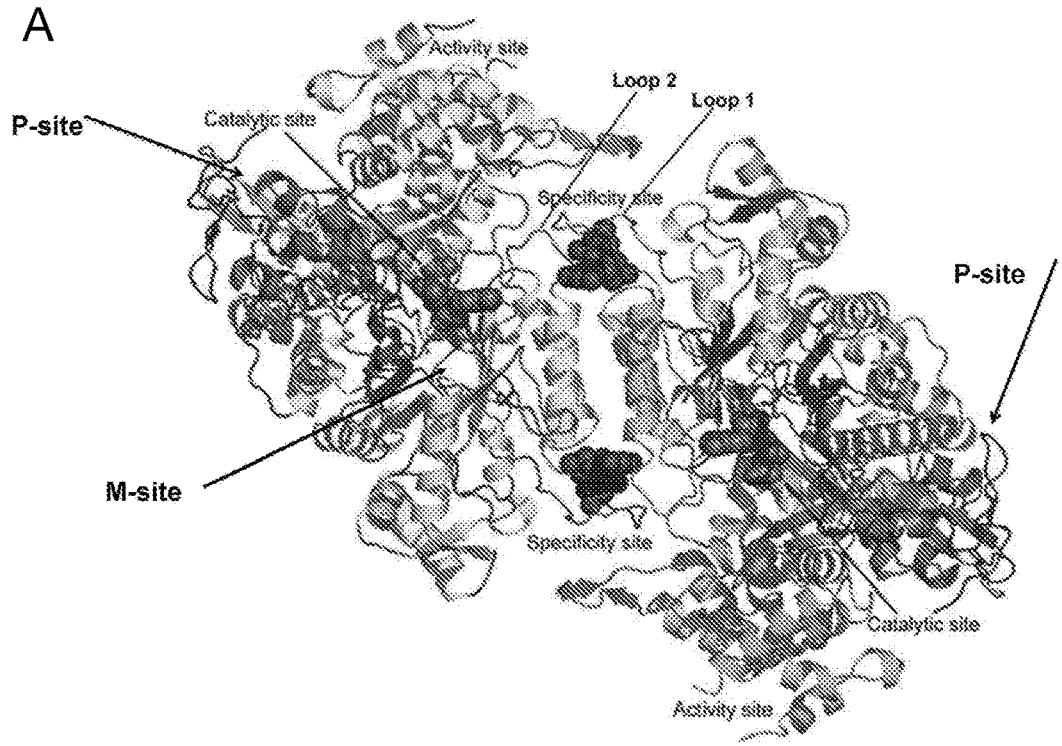
FIGS. 1(A-E) illustrate: (A) the structure of hRRM1 dimer with drug-target sites mapped. The M-site is the hexamer interface, the A-site controls activity, the S-site controls specificity, the C-site is the catalytic site, loop 1 and 2 mediate cross-talk between the S- and C-sites and the P-site binds the smaller $R^2$ subunit derived peptide. (B) and (C) illustrate tryptophan fluorescence quenching of hRRM1 in the presence of a phtalimide derivative and a hydrazone (NSAAH) respectively. (D) and (E) show no tryptophan fluorescence quenching of hRRM1 by compounds.
Figure 1B:
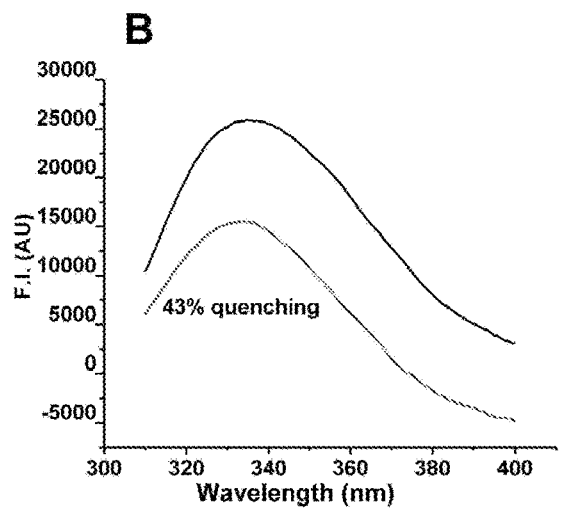
Figure 1C:
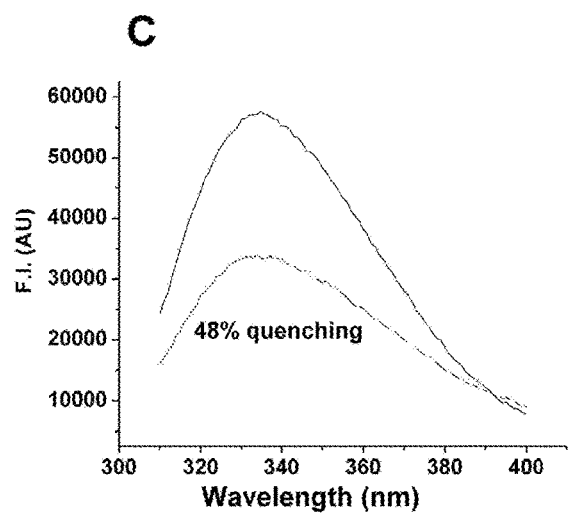
Figure 1D:
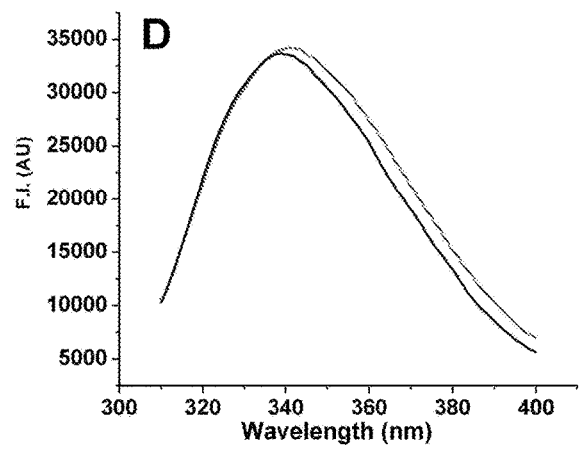
Figure 1E:
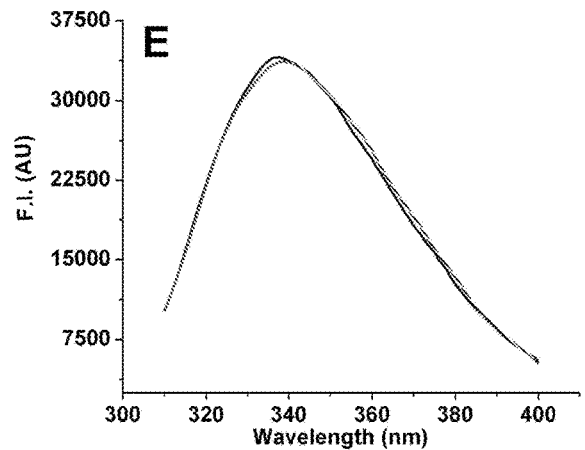

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.,", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g., sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "allosteric" refers to or denotes the alteration of the activity of a protein (e.g., an enzyme) through the binding of an effector molecule at a specific binding site. Effectors that decrease or increase the protein's activity are referred to as "allosteric modulators". An "allosteric site" as used herein relates to or denotes the site on an enzyme molecule which binds with a nonsubstrate molecule, inducing a conformational change that results in an alteration of the affinity of the enzyme for its substrate thereby modulating the enzyme's activity.

The phrase "having the formula" or "having the structure" is not intended to be limiting and is used in the same way that the term "comprising" is commonly used.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Non-limiting examples of hydrates include monohydrates, dihydrates, etc. Nonlimiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and al kylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S═O), a single bond without charges (S—O) or a single bond with charges [S(+)-O(−)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N+C—), cyanato (—O—CN), isocyanato (—ON+C—), isothiocyanato (—S—CN), azido (—N=N+=N—), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The term "anticancer agent" refers to a compound which treats a cancer (e.g., a compound which is useful in the treatment of a cancer). The anticancer effect(s) may arise through one or more mechanisms including, but not limited to, the regulation of cell proliferation, the inhibition of cell cycle progression, the inhibition of cell growth, the inhibition of angiogenesis, the inhibition of metastasis, the inhibition of invasion (e.g., the spread of tumor cells into healthy neighboring tissue), or the promotion of apoptosis. The term "antineoplastic" is used herein to mean a chemotherapeutic intended to inhibit or prevent the maturation and proliferation of neoplasms, by targeting the DNA.

The term "cell growth" is used in the contexts of cell development and cell division (reproduction). When used in the context of cell division, it refers to growth of cell populations, where one cell (the "mother cell") grows and divides to produce two "daughter cells" (M phase). When used in the context of cell development, the term refers to increase in cytoplasmic and organelle volume (GI phase), as well as increase in genetic material before replication (G2 phase).

The terms "neoplastic cell", "cancer cell" or "tumor cell" refer to cells that divide at an abnormal (i.e., increased) rate. A neoplastic cell or neoplasm (tumor) can be benign, potentially malignant, or malignant. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, meningoma, medulloblastoma, schwannoma and epidymoma.

The term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder (e.g., a neoplastic disorder). The term "patient" includes human and veterinary subjects. In some aspects of the disclosed methods, the subject has been diagnosed with a need for treatment of one or more neoplastic disorders prior to the administering step. In some aspects of the disclosed method, the subject has been diagnosed with a need for inhibition of ribonucleotide reductase enzyme activity prior to the administering step.

The terms "treating" or "treatment" of a condition may refer to alleviating a condition, slowing the onset or rate of development of a condition, reducing the risk of developing a condition, delaying the development of symptoms associated with a condition, reducing or ending symptoms associated with a condition, generating a complete or partial regression of a condition or some combination thereof. With regard to neoplastic disorders, "treating" or "treatment" may refer to inhibiting or slowing neoplastic and/or malignant cell growth, proliferation, and/or metastasis, delaying the development of neoplastic and/or malignant cell growth, proliferation, and/or metastasis, or some combination thereof. With regard to a tumor, "treating" or "treatment" may refer to eradicating all or part of a tumor, inhibiting or slowing tumor growth and metastasis, delaying the development of a tumor, or some combination thereof.

The phrase "therapeutically effective amount" refers to an amount of a compound that produces a desired therapeutic effect. In one aspect, the therapeutically effective amount is the amount required to inhibit neoplastic cell growth in the subject. The precise therapeutically effective amount is an amount of the composition that will yield the most effective results in terms of efficacy in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy (Gennaro ed. 22nd Edition, Pharmaceutical Press, London, UK, 2012).

The term "epitope" refers to a physical structure on a molecule that interacts with a selective component, e.g., the selective component such as an RRmod described herein. In exemplary embodiments, epitope refers to a desired region on a target molecule that specifically interacts with a selectivity component.

Embodiments described herein relate to ribonucleotide reductase modulators (RRmods), pharmaceutical compositions comprising RRmods, therapeutic uses of RRmods, as well as compounds found to be specifically effective as allosteric modulators of ribonucleotide reductase activity in neoplastic cells.

Ribonucleotide reductase enzyme activity is required for de novo DNA synthesis by catalyzing ribonucleotides to deoxy ribonucleotides and maintaining a balanced nucleotide precursor molecule pool. Since the proliferation of cancer cells requires excess dNTPs for DNA synthesis, it is believed that RRmods that specifically target RR1 can be employed to inhibit cell growth and proliferation of neoplastic cells through the modulation of ribonucleotide reductase enzyme activity.

It was found that the large subunit (α-subunit or hRRM1) of ribonuecleotide reductase (RR) includes four potentially druggable sites (see FIG. 1A). These sites include the A (activity)-site, the S (specificity)-site, the C (catalytic)-site and the P (peptide)-site. Using X-ray crystallography, an additional epitope of hRRM1, the M-site, was found to be in the hexamer interface of hRRM1. The M-site is a surface pocket including residues constituting the β-cap located on one dimer and the loop involving residue 480 belonging to an adjacent dimer at the hexamer interface.

It was found that the M-site can be targeted by small molecules to modulate ribonucleotide reductase activity. Using in silico high throughput screening and RR activity and growth inhibition cell culture in vitro assays, small molecules that bind to or complex with M-site or the catalytic C-site of hRRM1 were identified that were capable of allosterically inhibiting or activating the enzyme. These identified small molecules and analogs thereof can be used in a method of modulating ribonucleotide reductase activity in a neoplastic cell to inhibit neoplastic cell growth.

In some embodiments, RRmods described herein include agents capable of binding to or complexing with an epitope of hRRM1. In some embodiments the RRmod binds to the hexamer interface M-site or the catalytic C-site of hRRM1, and allosterically modulates ribonucleotide reductase enzyme activity, thereby affecting de novo DNA synthesis, cell growth and proliferation of neoplastic cells.

In certain embodiments, the RRmod is a small molecule. Exemplary data of small molecule compounds found to be specifically effective as allosteric modulators of ribonucleotide reductase activity are provided in the Examples below. In particular, the disclosed compounds had activity in inhibiting the ribonucleotide reductase activity in DNA synthesis assays and for killing carcinomas in a cell-based assay, generally with a micromolar $IC_{50}$.

In some embodiments, the RRmod can be a triazole. The triazole or analog thereof can have the formula (I):

(I)

wherein X is a triazole, (i.e., a heterocyclic compound having a five-membered ring of two carbon atoms and three nitrogen atoms);

A and Z are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, piperidine, pyridine, pyrazine, pyrimidine, pyridazine, groups incorporating amino acids or other moieties expected to bear positive or negative charge at physiological pH; and pharmaceutically acceptable salts thereof.

In some embodiments, X is selected from the group consisting of:

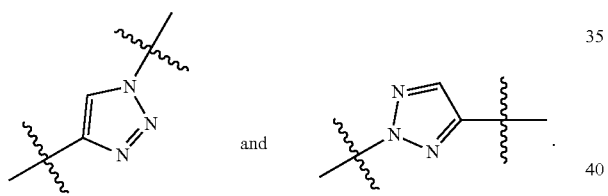

In some embodiments, A and Z are independently selected from the group consisting of:

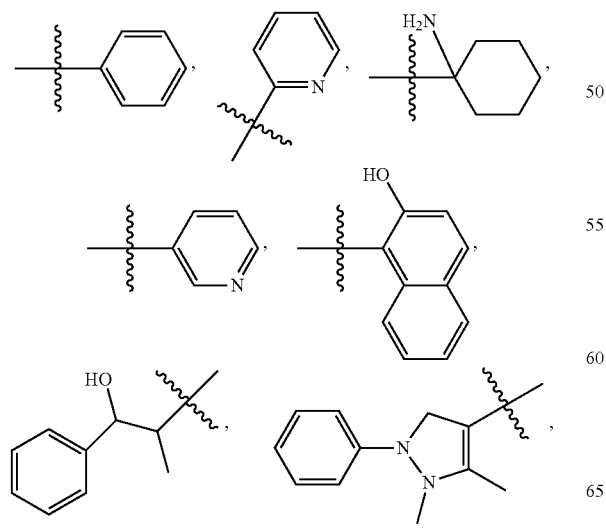

-continued

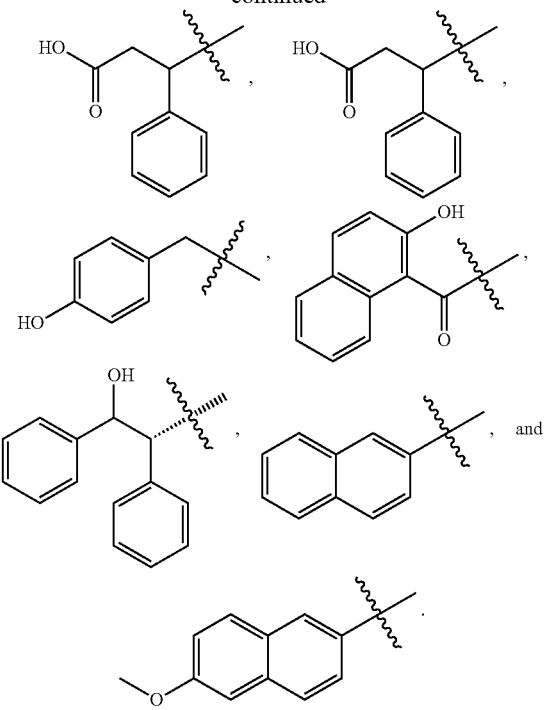

In certain embodiments, an RRmod having formula (I) can be selected from the group consisting of:

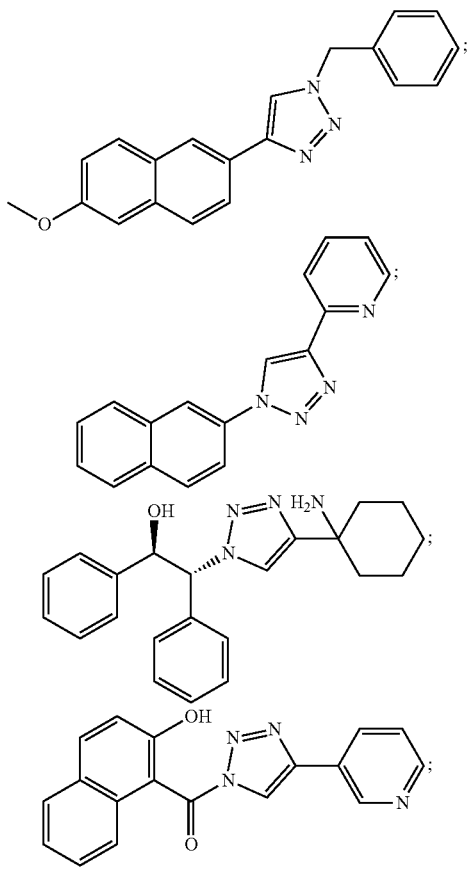

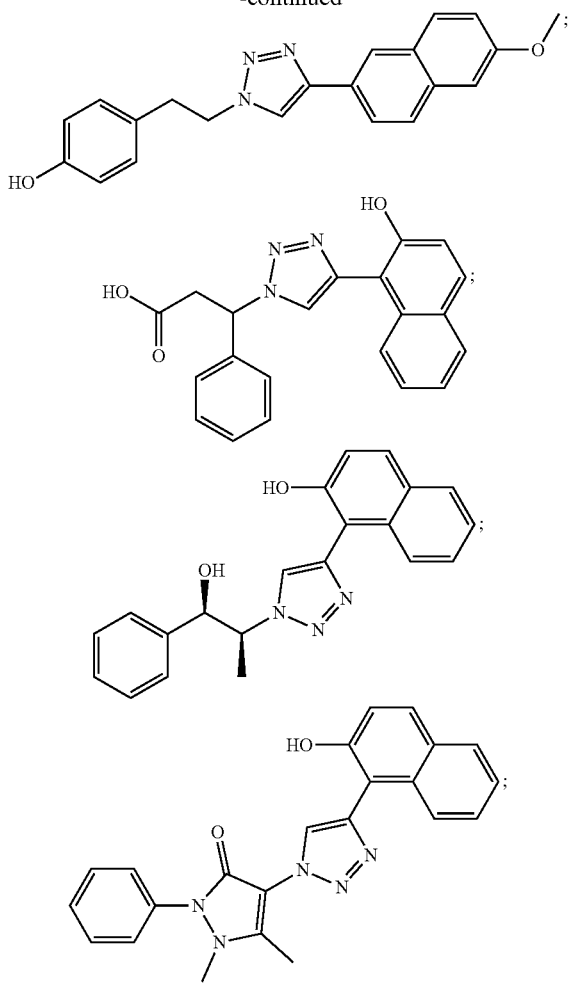

and pharmaceutically acceptable salts thereof.

In some embodiments the RRmod can be an oxadiazole or analog thereof. The oxadiazole can include a compound having the formula (II):

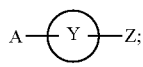

wherein Y is an oxadiazole;

A and Z are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, piperidine, pyridine, pyrazine, pyrimidine, pyridazine, groups incorporating amino acids or other moieties expected to bear positive or negative charge at physiological pH; and pharmaceutically acceptable salts thereof.

In some embodiments, Y is selected from the group consisting of:

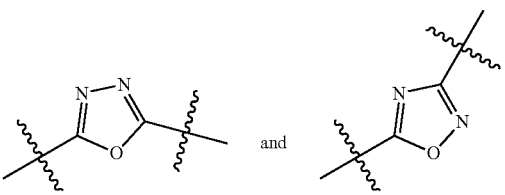

and

In other embodiments, the RRmod can be a oxadiazole or analog thereof having the have the formula (III):

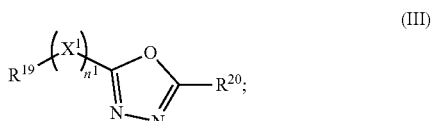

wherein $X^1$ is $CH_2$, COH, C=O, $CH_2$C=O, or $CH_2$CH($NH_2$);

$n^1$ is 0 or 1

$R^{19}$ and $R^{20}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, pyridine, groups incorporating amino acids or other moieties expected to bear positive or negative charge at physiological pH; and pharmaceutically acceptable salts thereof.

In other embodiments, the RRmod is an oxadiazole having the following formula (IV):
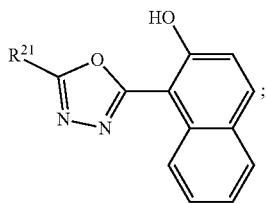
(IV)
wherein R$_{21}$ can be selected from the group consisting of:
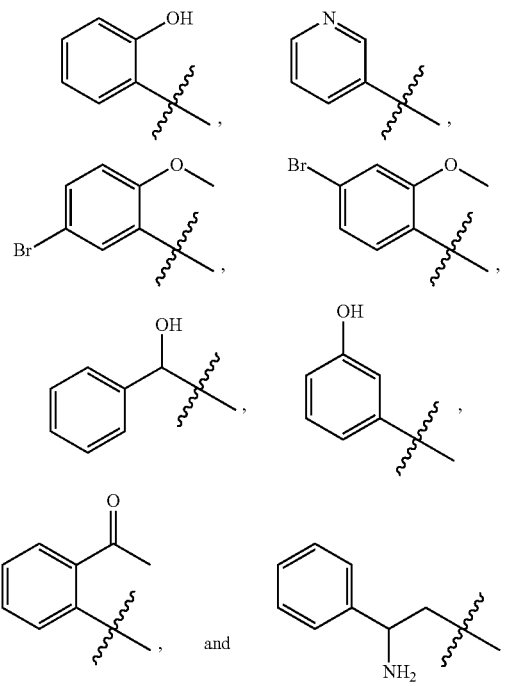
, and .
In certain embodiments, an RRmod having formula (III) can be selected from the group consisting of:
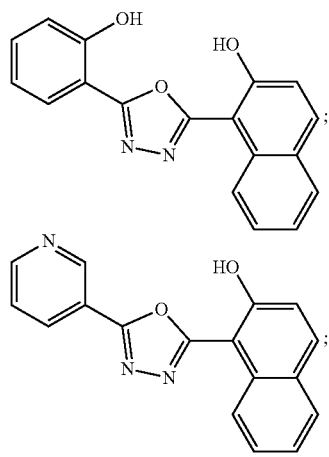
-continued
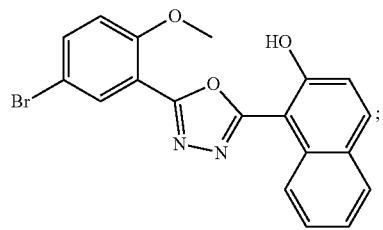
;
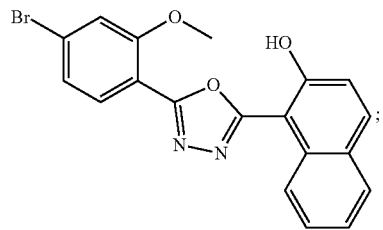
;
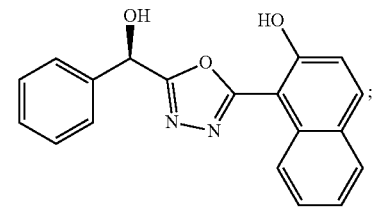
;
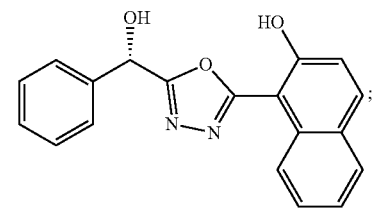
;
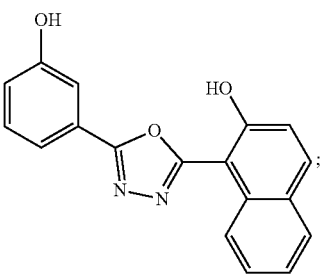
;
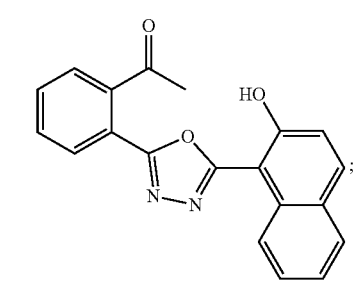
;
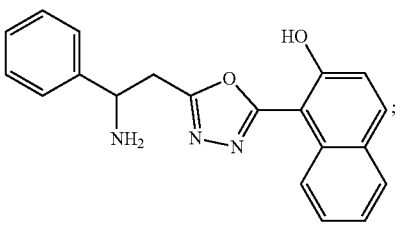
;
and pharmaceutically acceptable salts thereof.

In other embodiments, the RRmod is an oxadiazole having the following formula (V):

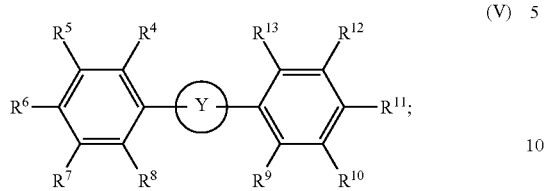

wherein Y is an oxadiazole (i.e., a heterocyclic compound having a five-membered ring of two carbon atoms, one oxygen atom and two nitrogen atoms);

$R^4$ to $R^{13}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, pyridine, groups incorporating amino acids or other moieties expected to bear positive or negative charge at physiological pH; and pharmaceutically acceptable salts thereof, wherein adjacent R groups can be linked to form a cyclic or polycyclic ring, wherein the ring is a substituted or unsubstituted aryl, heteroaryl, cycloalkyl or heterocyclyl.

In other embodiments, the RRmod is an oxadiazole having the following formula (VI):

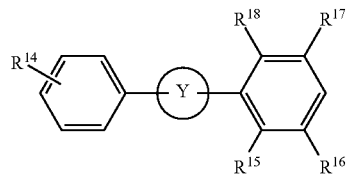

wherein Y is an oxadiazole;
$R^{14}$ is H, OH or a halogen; and
$R^{15}$ to $R^{18}$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, cycloalkyl, heterocyclyl, heterocloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, pyridine, groups incorporating amino acids or other moieties expected to bear positive or negative charge at physiological pH; and pharmaceutically acceptable salts thereof, wherein $R^{15}$ and $R^{16}$ or $R^{17}$ and $R^{18}$ can be linked to form a cyclic or polycyclic ring, wherein the ring is a substituted or unsubstituted aryl, heteroaryl, cycloalkyl or heterocyclyl.

Additional RRmods can be identified by screening compounds for the ability to modulate (e.g., inhibit or activate) ribonucleotide reductase enzyme activity. Candidate RRmods can be screened for function by a variety of techniques known in the art and/or disclosed within the instant application. Candidate compounds may be screened individually, in combination, or as a library of compounds.

Candidate compounds screened include chemical compounds. In some aspects, the candidate compound is a small organic molecule having a molecular weight of more than about 50 and less than about 2,500 daltons. Compounds screened are also found among biomolecules including, but not limited to: peptides, saccharides, fatty acids, steroids, pheromones, purines, pyrimidines, derivatives, structural analogs or combinations thereof. The compounds screened can include functional groups necessary for structural interaction with proteins, particularly hydrogen bonding, and typically include at least an amine, carbonyl, hydroxyl, or carboxyl group.

Candidate compounds can be obtained from a wide variety of sources including libraries of synthetic or natural compounds. Compounds to be screened can be produced, for example, by bacteria, yeast or other organisms (e.g., natural products), produced chemically (e.g., small molecules, including peptidomimetics), or produced recombinantly. It is further contemplated that natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In many drug screening programs, with test libraries of compounds and natural extracts, high throughput assays are desirable in order to maximize the number of compounds surveyed in a given period of time. Assays described herein may be developed with purified or semi-purified proteins or with lysates. These assays are often preferred as "primary" screens in that they can be generated to permit rapid development and relatively easy detection of an alteration in a molecular target, which is mediated by a test agent. Assays described herein can include cell-based assays. Cell-based assays may be performed as either a primary screen, or as a secondary screen to confirm the activity of compounds identified in a cell free screen, such as an in silico screen.

Embodiments described herein also relate to a method of screening in silico for a compound effective as an RRmod.

For example, a 3-D model of the hexamer interface epitope of RR1 targeted by small molecules can be used to provide a pharmacophore using X-ray Crystallography. An initial model can then be generated using a suitable protein modeling software program. In some aspects, the model can then be subjected to energy refinement with a software program such as SURFLEX dock. The pharmacophore can be modified to comply to the Lipinski limits to design drug-like molecules with good bioavailability. In one embodiment, the template used for docking was the hexamer interface of ribonucleotide reductase as shown in FIG. 1.

Once a model is built, small molecule RRmods that bind to ribonucleotide reductase at the hexamer interface of RR1 can be identified by methods well known in the relevant art using in silico conformation screening techniques. For example, virtual screening of the University of Cincinnati Drug Discovery Center (UC DCC) Library of 350,000 compounds can be performed using the drug discovery software SYBYLX1.3 (Tripos, St. Louis, Mo.). Such software can also be used to design modified analogs of compounds for use as RRmods. In parallel, ZINC and other commercial databases can be searched using within SYBYLX1.3 software for lead compounds that satisfy the pharmacophore. These hits can be docked and scored using SURFLEX dock option in SYBYLX1.3. The best hits can then be discriminated using two scoring functions called, a docking score and the C-score. The docking score is theoretically equivalent to the negative logarithm of $K_d$, while C-score is a consensus scoring function. Hence, docking scores that are equal to 6 would mean a theoretical $K_d$ of micromolar. The maximum C-score that can be obtained is five. Based on these criteria, after virtually screening the library, the best scoring candidates can be selected and then tested using various in vitro and cell based assays described herein and known in the art for efficacy. The larger numbers obtained for dock score and C-scores greater than 6 and 4-5 respectively represents the high ranking inhibitors that are predicted to have high affinities.

In some aspects, about 20,000 compounds can be selected from in silico screening for an in vitro high-throughput screening (HTS). HTS can be carried out using an automated HTS system which performs biochemical and cell-based assays using 96 or 384-well microtiter plates. The system includes detectors, $CO_2$ incubators, pipetting systems, a plate washer, centrifuge, a storage unit, bar code readers, xyz robots, turntables, and pushers necessary for fully automated screening. A Jobin Yvon-Spex fluorescence spectrophotometer can be used to record the spectra. Alternatively, a multimode PERKIN-ELMER plate reader can be used for detecting fluorescence intensity, fluorescence polarization, fluorescence resonance energy transfer, luminescence, or absorbance using ZEISS optics and a sensitive CCD camera. The PERKIN-ELMER Opera detector performs high content screening using confocal microscopy and image analysis software powered by onboard servers. Lasers and CCD cameras allow measurement of subcellular localization, binding events or any other microscopic images which can be rapidly quantitated. Image analysis is performed immediately after the image is captured and stored in a database. All other data can be analyzed using GENEDATA HTS analysis software (Switzerland), stored in a GENEDATA database based on ORACLE.

In some embodiments, in vitro HTS includes a fluorescence based assay adapted for HTS. For example, in vitro HTS can employ tryptophan fluorescence quenching. The binding sites of proteins are known to often contain tryptophan (Trp) residues, whose fluorescent properties may be altered upon ligand binding. Conformational changes within the binding site or simply the presence of the ligand can result in either fluorescence quenching or enhancement, which may be utilized to quantitatively investigate protein-ligand interactions. Change in intrinsic tryptophan fluorescence is used to measure the binding of a candidate agent to a targeted binding site of ribonucleotide reductase. The trytophan fluorescence spectra of Hurl (Human ribonucleotide reductase) and a candidate compound can be recorded and then compared in order to determine the extent of quenching. The ribonucleotide reductase samples can be titrated with 65 µM candidate compounds at room temperature where a decrease in fluorescence, or quenching, can be correlated with the binding affinity of the candidate compound to the targeted binding site of ribonucleotide reductase and/or a conformational change in the targeted ribonucleotide reductase binding site.

In some aspects, candidate RRmod compounds, including those collected from an in silico similarity search or HTS assay, may be further screened for efficacy using in vitro and/or in vivo experimental screening methods known in the art. The efficacy of an identified compound can be assessed by generating dose response curves from data obtained using various concentrations of the test compound. Moreover, a control assay can also be performed to provide a baseline for comparison. Such candidates can be further tested for their effects on cancer and tumor cell growth, proliferation, apoptosis, differentiation, and transformation properties compared to controls as well as their ability to: inhibit de novo DNA synthesis in vitro; unbalance nucleotide pool of DNA precursor molecules in vitro; modulate ribonucleotide reductase activity in vitro; and/or for other properties, such as the ability to inhibit cell growth and increase the toxicity of neoplastic cells in vivo.

In some embodiments, assays used for in vitro screening of candidate compounds for cell growth inhibition can include DNA synthesis assays and MTT colorimetric assays to measure cell metabolism. For example, a DNA synthesis assay can include the steps of: (a) contacting the neoplastic cell with various concentrations of a candidate compound; and (b) comparing the DNA synthesis of the cell in step (a) with the DNA synthesis of the cell in the absence of the compound so as to determine whether the compound significantly inhibits ribonucleotide reductase activity, thereby reducing the growth of the cell. One can also determine the $IC_{50}$ of a candidate compound if the compound is found to significantly inhibit ribonucleotide reductase activity. The $IC_{50}$ of a drug can be determined by constructing a dose-response curve and examining the effect of different concentrations of a candidate agent on cell growth and/or ribonucleotide reductase enzyme activity. $IC_{50}$ values can be calculated for a given compound by determining the concentration needed to inhibit half of the maximum biological response of the compound.

For in vivo screening of candidate compounds, the candidate compound can be administered in any manner desired and/or appropriate for delivery of the compound in order to affect a desired result. For example, the candidate compound can be administered to a mammalian subject by injection (e.g., by injection intravenously, intramuscularly, subcutaneously, or directly into the tissue in which the desired affect is to be achieved), topically, orally, or by any other desirable means.

Normally, this screen will involve a number of animals receiving varying amounts and concentrations of the candidate compounds (from no compound to an amount of compound that approaches an upper limit of the amount that can be delivered successfully to the animal), and may include delivery of the compound in different formulations. The compounds can be administered singly or can be combined in combinations of two or more, especially where administration of a combination of compounds may result in a synergistic effect.

The effect of compound administration upon the animal model can be monitored by any suitable method such as assessing the number and size of tumors, overall health, survival rate, etc. A candidate compound is identified as an effective compound for use in the treatment of a neoplastic disorder in a subject where candidate compound inhibits neoplastic cell growth in the animal in a desirable manner (e.g., by binding to the Sml1 allosteric binding site of ribonucleotide reductase and allosterically inhibiting the enzyme's activity, etc.). In some aspects, effective compounds can be identified as having low toxicity in vivo.

As shown in the Examples below, RRmods disclosed herein have been shown to bind to epitopes (e.g., M-site or C-site) of the large α-subunit of RR1 and inhibit growth of multiple cancer cell types in vitro, supporting the use of these RRmods to treat a wide range of neoplastic diseases and disorders. Thus, in accordance with another embodiment, RRmods described herein can be used for the preparation of a pharmaceutical composition for the treatment of a neoplastic disorder in a subject. In one embodiment, the subject is suffering from a neoplastic disorder characterized by increased cell growth. In another embodiment, the subject is suffering from cancer.

A therapeutically effective amount of an RRmod described herein can be administered to a subject for the treatment of a variety of conditions in order to inhibit cell growth in the subject. Such conditions include, without being limited thereto, neoplastic disorder, and in particular all types of solid tumors; skin proliferative diseases (e.g., psoriasis); and a variety of benign hyperplasic disorders.

In one aspect, the neoplastic disorder is cancer. The cancer can include, but is not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, meningoma, medulloblastoma, schwannoma and epidymoma. In certain aspects, the cancer is a pancreatic, breast, lung, colon or glyoblastoma cancer.

In another aspect, the neoplastic disorder is a solid tumor. Exemplary solid tumors include carcinomas, sarcomas, adenomas, and cancers of neuronal origin and if fact to any type of cancer which does not originate from the hematopoeitic cells and in particular concerns: carcinoma, sarcoma, adenoma, hepatocellular carcinoma, hepatocellularcarcinoma, hepatoblastoma, rhabdomyosarcoma, esophageal carcinoma, thyroid carcinoma, ganglioblastoma, fibrosarcoma, myxosarcoma, liposarcoma, cohndrosarcoma, osteogenic sarcoma, chordoma, angiosarcoma, endotheliosarcoma, lymphagiosarcoma, synovioama, Ewing's tumor, leimyosarcoma, rhabdotheliosarcoma, colon carcinoma, pancreatic cancer, breast cancer, ovarian cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small lung carcinoma, bladder carcinoma, epithelial carcinoma, glioma, astrocyoma, medulloblastoma, craniopharyngioma, ependynoma, pinealoma, retinoblastoma, multiple myeloma, rectal carcinoma, thyroid cancer, head and neck cancer, brain cancer, cancer of the peripheral nervous system, cancer of the central nervous system, neuroblastoma, cancer of the endometrium, as well as metastasis of all the above.

Benign hyperplasic disorders include, without being limited thereto, benign prostate hyperplasia (BPH), non-tumorigenic polyps in the digestive tract, in the uterus and others.

In addition to cancer, the RRmods disclosed herein may be used to treat other conditions associated with aberrant ribonucleotide reductase enzyme activity such as for example various mitochondrial, redox-related, degenerative diseases, and viruses such as HIV.

When used as therapeutic agents in the treatment of neoplastic disorders, the RRmods can be conveniently formulated into pharmaceutical formulations composed of one or more of the compounds (e.g., RRmods of formulas (I-II) or an RRmod identified by a screening assay as described above) in association with a pharmaceutically acceptable carrier or excipient. (See Remington: The Science and Practice of Pharmacy (Gennaro ed. 22nd Edition, Pharmaceutical Press, London, UK, 2012), which discloses typical carriers and conventional methods of preparing pharmaceutical formulations).

In making the compositions, the RRmod is usually mixed with the excipient, diluted by an excipient or enclosed within a carrier which can be in the form of a capsule, sachet, paper or other container. When the excipient serves as a diluent, it can be a solid, semi-solid, or liquid material, which acts as a vehicle, carrier or medium for the RRmod. Thus, the compositions can be in the form of tablets, pills, powders, lozenges, sachets, cachets, elixirs, suspensions, emulsions, solutions, syrups, aerosols (as a solid or in a liquid medium), soft and hard gelatin capsules, suppositories, sterile injectable solutions, and sterile packaged powders. The RRmods can also be administered to a subject as a stabilized prodrug to increase the activity, bioavailability, stability or otherwise alter the properties of the RRmod.

The effective amount of RRmod in the pharmaceutical composition and unit dosage form thereof may be varied or adjusted widely depending upon the particular application, the manner or introduction, the potency of the particular compound, and the desired concentration.

The effective amount is typically determined in appropriately designed clinical trials (dose range studies) and the person versed in the art will know how to properly conduct such trials in order to determine the effective amount. As generally known, an effective amount depends on a variety of factors including the affinity of the RRmod to the targeting binding site (e.g., the M-site or C-site of hRRM1), its distribution profile within the body, a variety of pharmacological parameters such as half life in the body, on undesired side effects, if any, on factors such as age and gender, etc.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In this case, the composition will typically be administered over an extended period of time in a single daily dose, in several doses a day, as a single dose and in several days, etc. The treatment period will generally have a length proportional to the length of the disease process and the specific RRmod effectiveness and the patient species being treated.

RRmods and pharmaceutical compositions thereof can be administered to the subject by any suitable means, including, for example, oral, intravenous, intramuscular, intra-arterial, subcutaneous, intranasal, via the lungs (inhalation) and through local administration.

RRmods described herein can be used as single agents or in combination or in conjunction with one or more other therapeutic agents in the treatment of the aforementioned diseases, disorders and conditions for which RRmods or the other agents have utility. In some embodiments, a combination of an RRmod and other therapeutic agent together is safer or more effective than either drug alone.

In some embodiments, the other therapeutic agent used in a combination therapy can include at least one anti-proliferative agent selected from the group consisting at least one of a chemotherapeutic agent, an anticancer agent, an antimetabolite, a DNA damaging agent, an antitumorgenic agent, an antimitotic agent, an antiviral agent, an antineoplastic agent, an immunotherapeutic agent, and a radiotherapeutic agent. Additional therapeutic agents used in combination therapies with RRmods can include biguanides (e.g., metformin, phenformin and buformin), AP endonuclease inhibitors (e.g., methoxyamine (MX)), BER inhibitors including PARP inhibitors, and ribonucleotide reductase inhibiting agents. Exemplary ribonucleotide reductase inhibiting agents for use in conjunction with RRmods include $O^6$-methyl-arabinofuranosyl guanine (nelarabine), 2'-fluro-2'-deoxyarabinofuranosyl-2-chloroadenine (clofarabine), $N^4$-pentyloxycarbonyl-5'-deoxy-5-flurocytidine (capecitabine), 2,2-difluoro-2'-deoxyadenosine (cladribine), arabinofuranosyl-2-fluoroadenine (fludarabine), 2'-deoxycoformycin (pentostatin), 5-fluro-2'deoxyuridine, arabinofuranosylcytosine (cytarabine), 6-thioguanine, 5-fluorouracil, methotrexate, 6-mercaptopurine.

In some aspects, RRmods can be used in a combination therapy with an anti-proliferative agent. The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which can be included by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endotheliai cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

A first family of anti-proliferative agents, which may be used in combination therapy with an RRmod consists of antimetabolite-type anti-proliferative agents. Antimetabolites are typically reversible or irreversible enzyme inhibitors, or compounds that otherwise interfere with the replication, translation or transcription of nucleic acids. Examples of antimetabolite antineoplastic agents that may be used include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, gemcitabine, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

A second family of anti-proliferative agents, which may be used in combination therapy with the RRmods, consists of alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Examples of alkylating-type anti-proliferative agents that may be used include, but are not limited to, Shionogi 254-S, aldo-phosphamide analogs, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide (TMZ), teroxirone, tetraplatin and trimelamol.

A third family of anti-proliferative agents that may be used in combination therapy with the RRmods consists of antibiotic-type anti-proliferative agents. Examples of antibiotic-type anti-proliferative agents that may be used include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of anti-proliferative agents that may be used in combination therapy with the RRmods consists of synthetic nucleosides. Several synthetic nucleosides have been identified that exhibit anticancer activity. A well known nucleoside derivative with strong anticancer activity is 5-fluorouracil (5-FU). 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381, which is herein incorporated by reference in its entirety. Further 5-FU derivatives have been described in the following patents listed in JP 50-50383, JP 50-50384, JP 50-64281, JP 51-146482, and JP 53-84981 hereby individually incorporated by reference herein. Further synthetic nucleoside analogs include 4-amino-1-(2-deoxy-b-D-erythro-pentofuranosyl)-1,3,5-triazin-2(1H)-one (e.g., 5-aza-21-deoxycytidine, decitabine, or DACOGEN, Eisai Inc., Woodcliff Lake, N.J.). Other examples, of nucleoside analogs that can be used to treat cancer are listed in U.S. Pat. No. 4,000,137, which is incorporated herein by reference, Cytosine arabinoside (also referred to as Cytarabin, araC, and Cytosar) and 5-Azacytidine (VIDAZA, Celegene Corp., Summit, N.J.).

A fifth family of anti-proliferative agents that may be used in combination therapy with the RRmods consists of hormonal agents. Examples of hormonal-type anti-proliferative agents that may be used include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; epristeride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKSO1; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

A sixth family of anti-proliferative agents that may be used in combination therapy with the RRmods consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW 502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI 941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin®, Cell Pathways Exisulind® (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR 63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K 477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY 186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N (retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org 10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium(selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

In the instances of combination therapies described herein, it will be understood the administration further includes a pharmaceutically or therapeutically effective amount of the additional therapeutic agent in question. The second or additional therapeutic agents described herein may be administered in the doses and regimens known in the art or may be administered in low doses.

In some embodiments, the administration of a RRmod and an additional therapeutic agent can result in a synergistic effect. A "synergistic effect" as used herein means the combined effect of two or more therapeutic agents can be greater than the sum of the separate effects of the agents alone. For example, the combined effect of an RRmod, and an anticancer agent, such as metformin or another RRmod such as gemcitabine, can be greater than the sum of the separate effects of a single RRmod and metformin or gemcitabine alone.

In some embodiments, the combined effect of administering two or more RRmod compounds is greater than the sum of the separate effects of the RRmods alone. In certain embodiments, a NSAAH hydrazone RRmod, as described in PCT Application No. PCT/US2016/065928, the subject matter of which is incorporated herein by reference in its entirety, can be administered in combination with one or more triazole or oxidiazole RRmods describe herein to produce a synergistic therapeutic effect. In a particular embodiment, a NSAAH RRmod and an oxidiazole RRmod selected from the group consisting of Oxa A, Oxa F and Oxa N, can be administered in combination with an oxidiazole RRmod to produce a synergistic therapeutic effect (see Table 3). In an exemplary embodiment, a NSAAH RRmod and the oxidiazole RRmod Oxa F can be administered in combination to produce a synergistic therapeutic effect.

Where the combined effect of administering a RRmod and another therapeutic agent is greater than the sum of the separate effects of the RRmod and the other agent alone, the RRmod and/or therapeutic agent can be administered to the subject in a lower dose or even a sub-therapeutic dose. A benefit of lowering the dose of the combination therapeutic agents and therapies can include a decrease in the incidence of adverse effects associated with higher dosages. For example, by the lowering the dosage of a chemotherapeutic agent such as methotrexate, a reduction in the frequency and the severity of nausea and vomiting will result when compared to that observed at higher dosages.

The additional therapeutic agent can be administered by a route and in an amount commonly used therefore, contemporaneously or sequentially with a RRmod compound. When administered as a combination, a RRmod compound and additional therapeutic agent(s) can be formulated as separate compositions which are given at the same time or different times, or the therapeutic agents can be given as a single composition.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Reversible Triazole-Based RR Modulators Inhibiting the Catalytic Site for the Treatment of Cancer Introduction Ribonucleotide reductase is a multi-protein enzyme consisting of a large subunit called hRRM1 containing the catalytic sites and allosteric sites and a small subunit called hRRM2 that houses the free radical required for initiating radical-based chemistry (FIG. 1A) (references). The hRRM1 subunit catalyzes the conversion of four ribonucleoside diphosphates (UDP, CDP, GDP and ADP) to their respective deoxy forms. During the S-phase of the cell cycle, these reduction reactions are allosterically controlled by binding of nucleotide triphosphates to two different sites on RR (Brown and Reichard and others). The S-site is located at the dimer interface of hRRM1 and is involved in allosterically regulating substrate binding specificity (FIG. 1A). ATP activates the enzyme by binding at the A-site while dATP inactivates the enzyme by binding at the A-site. (FIG. 1A).

Recent studies with RR have revealed the importance of oligomerization and its regulation. By convention the hRRM1 subunit is referred to as α and the hRRM2 subunit as β. Although the multimerization of RR is still a subject of investigation, the prevailing model is that RR minimally functions as an $\alpha_2\beta_2$ complex. At physiological concentrations of ATP (3 mM) RR exists predominantly as a hexamer with a small population of dimer present. When dATP is bound, the large subunit has been shown to exist as a dimer and hexamer, while baculovirus expressed mouse RR1 was observed to exist as a tetramer. Recently, hexamer formation has been shown to be important for drugs such as gemcitabine and clofarabine binding to RR. For example, gemcitabine was shown to inactivate hRRM1 by inducing α6β6 oligomers while clofarabine was shown to bind hRRM1 hexamers with nanomolar affinity. While this drug was shown to induce hRRM1 dimers, it is unable to induce the formation of hexamers, leading the authors to conclude that 5-NINTP loses its inhibitory potency due to its inability to form hexamers.

We previously characterized the hydrazone compound NSAAH (Naphthyl Salicyl Acyl Hydrazone) that inhibits hRR reversibly with micromolar affinity in vitro. The crystal structure of the NSAAH complex with hRR together with steady state kinetic data demonstrated that it binds in the C-site of hRRM1 (See FIG. 1). Importantly, the $IC_{50}$ for NSAAH was within two fold of that of Gemcitabine for growth inhibition of multiple cancer cell lines. However, NSAAH demonstrated little measurable cytotoxicity against normal mobilized peripheral blood progenitor cells. Thus, these data identified the first non-nucleoside competitive inhibitor of hRRM1, and reveal its improved in vivo inhibition properties relative to existing therapeutics providing a starting point for rational fragment-based drug design of a new class of hRR inhibitors.

We examined the structure of the hydrazone bound to the catalytic site (C-site) of RR1. The mode of binding of the hydrazone moiety was postulated to be replaced by a triazole as the geometry and stereochemistry would be retained. Furthermore, the triazole permits the feasibility of click chemistry, enabling multiple substitutions to create diversity libraries. The hypothesis was tested by designing and modeling several traizole derivatives using the docking software Schrödinger, which predicted favorable binding to the hRRM1 active site. Initially, eight triazole derivatives were synthesized and tested using the RR radioactivity assay for inhibition. Table 1 shows the initial data.

Figure 2:
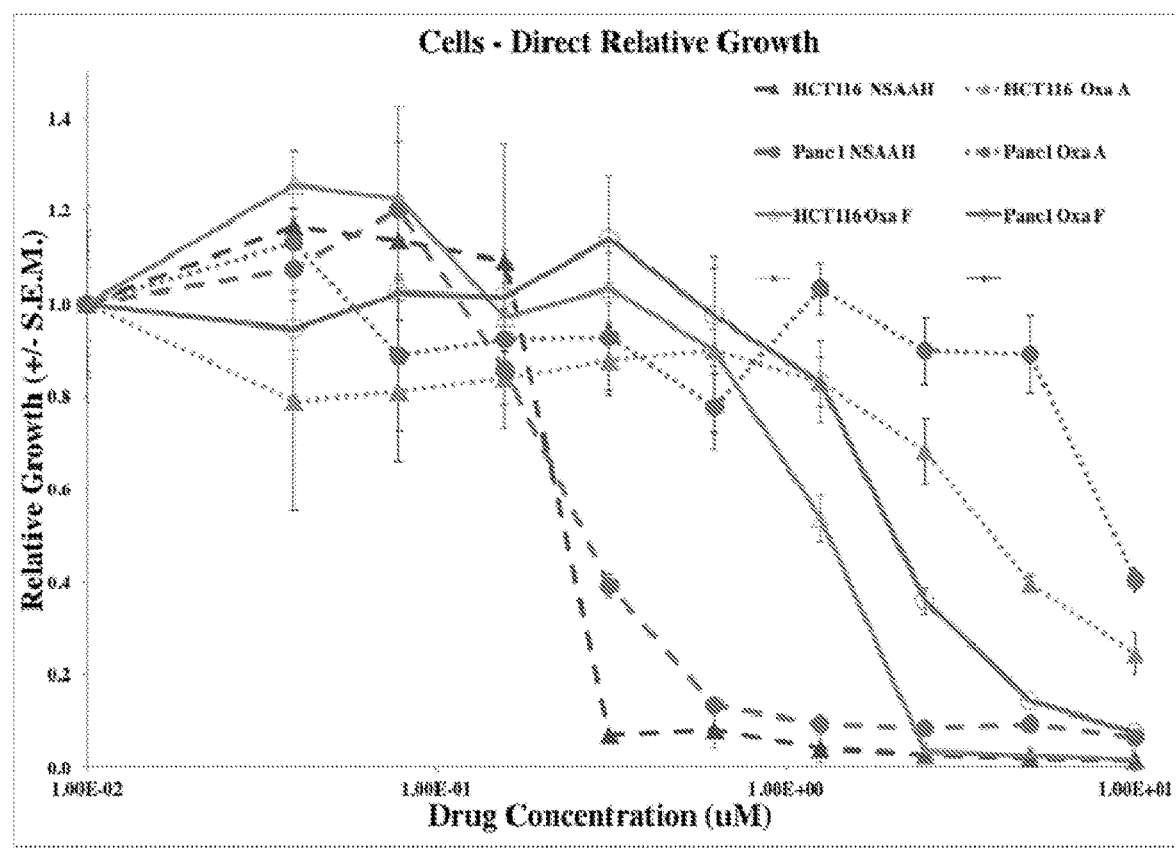
FIG. 2 is a graphical illustration showing the results of detailed growth inhibition studies in the screened cell lines (HCT116 & Panc1) for two of the oxadiazole compounds, OXA A and OXA F, where each had activity in the low micromolar range. The previously identified hydrazone RRmod NSAAH was included as a comparator positive control in the studies.

In a second series of experiments the hydrazone was replaced by an oxadiazole, a five-membered ring that is also an excellent replacement. A small library consisting of the napthyl moiety conjugated to the oxidiazole followed by benzene substitutions including pyridine's were synthesized and tested in cell growth inhibition assays against the HTC116 cell line and the Panc1 cell line. Based on the few compounds tested so far OXA A and OXA F had activity in the low micromolar range (see Table 2 and FIG. 2).

TABLE 1

Identification of eight novel hRRM1 inhibitors using in silico docking, and growth inhibition

| Structure | Cellular $IC_{50}s$ HCT-116 Panc 1 |
|---|---|
| (NSAAT A) | No cytotoxicity |
| (NSAAT B) | Not tested |

TABLE 1-continued

Identification of eight novel hRRM1 inhibitors using in silico docking, and growth inhibition

| Structure | Cellular IC$_{50}$s HCT-116 Panc 1 |
|---|---|
| (NSAAT E) | No cytotoxicity |
| (NSAAT F) | No cytotoxicity |
| (NSAAT G) | No cytotoxicity |
| (NSAAT H) | No cytotoxicity |
| (NSAAT I) | No cytotoxicity |

TABLE 1-continued
Identification of eight novel hRRM1 inhibitors using in silico docking, and growth inhibition
| Structure | Cellular IC$_{50}$s HCT-116 Panc 1 |
|---|---|
| 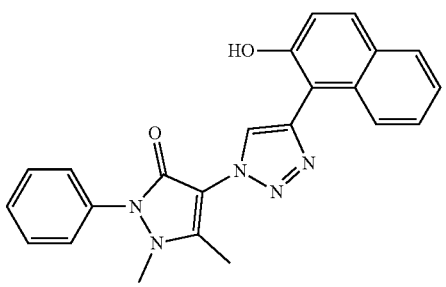 (NSAAT J) | No cytotoxicity |
TABLE 2
Identification of nine novel hRRM1 inhibitors using in silico docking, and growth inhibition
| Structure | Cellular IC$_{50}$s | |
|---|---|---|
| | HCT-116 | Panc 1 |
| 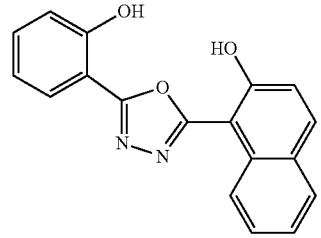 (OXA A) | 3.2 µM | 7 µM |
| 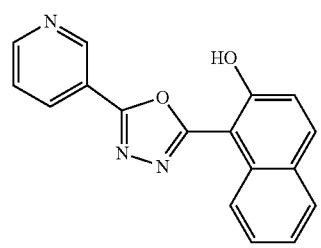 (OXA F) | 1.2 µM | 2.5 µM |
| 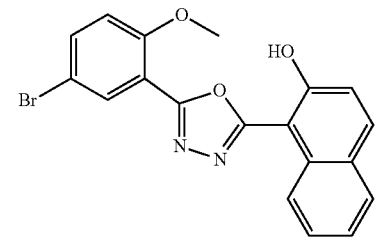 (OXA V) | — | — |

TABLE 2-continued
Identification of nine novel hRRM1 inhibitors using in silico docking, and growth inhibition
| Structure | Cellular IC$_{50}$s | |
| --- | --- | --- |
| | HCT-116 | Panc 1 |
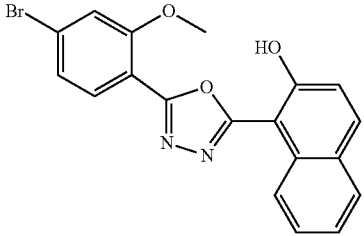
(OXA W) | — | —
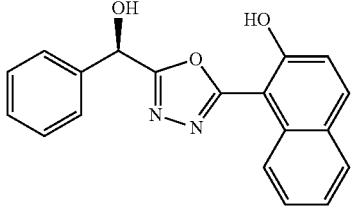
(OXA M$^+$) | — | —
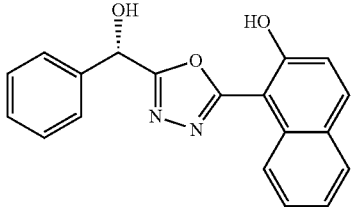
(OXA M$^-$) | — | —
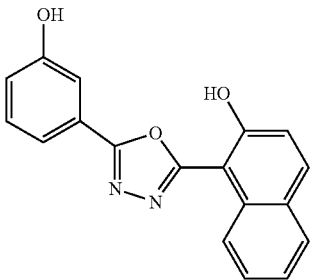
(OXA H) | — | —
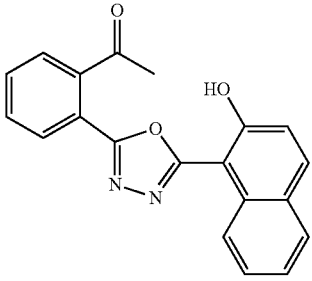
(OXA B) | — | —

TABLE 2-continued

Identification of nine novel hRRM1 inhibitors using in silico docking, and growth inhibition

| | Cellular IC$_{50}$s | |
|---|---|---|
| Structure | HCT-116 | Panc 1 |
| (OXA D) | — | — |

Material and Methods

Triazole Synthesis

Triazoles are synthesized using click chemistry. Iodination of 2-napthol under acidic conditions followed by Sonogashira coupling with TMS-acetylene provided 1-((trimethylsilyl)ethynyl)naphthalene-2-ol. Removal of the trimethylsilyl group by methanol produced the terminal alkyne required for click chemistry (1-ethynylnaphthalen-2-ol). Aryl azides were produced by converting primary amines to diazoniums and subsequent treatment with sodium azide. A 1:1.02 stoichiometric reaction of 1-ethynylnaphthalen-2-ol with aryl azide under Sharpless click conditions produced the desired triazole compounds. The crude product is collected by vacuum filtration and purified by flash column chromatography (silica gel, 15% Ethyl Acetate/Hexanes).

Oxadiazole Synthesis

Oxadiazoles are produced by refluxing acyl hydrazones in DMSO in the presence of excess iodine (1.2 equivalents) and $K_2CO_3$ (3 equivalents). The reaction is diluted by 20 in 5% $N_2S_2O_3$(aq), then extracted with ethyl acetate (5×20 mLs). The organic solutions are back extracted with water (3×15 mLs), dried by MgSO4, filtered, and concentrated en vacuo to collect the crude product. Compounds are purified by flash column chromatography (silica gel, 10% Ethyl Acetate/Hexanes).

Protein Expression and Purification of hRRM1

The hRRM1 protein was expressed in *E. coli* BL21 DE3 (RIL) and purified using peptide affinity chromatography, as described previously. The homogeneous protein was pooled and concentrated to 20-25 mg/ml, as quantified by UV absorbance spectroscopy, as described previously.

Establishing Reversible Inhibition of NSAAH of hRR

In assay buffer, 50 μM NSAAH was incubated on ice with 2.5 μmol of hRRM1 for 30 minutes. The assay sample was then diluted by a factor of 5, and enzyme activity was assayed in triplicate. As a control, the assay was also performed for non-drug-treated hRRM1 and for hRRM1 with 50 μM NSAAH without dilution.

Crystallization and Data Collection

20 mg/ml hRRM1 protein was incubated with 20 mM dTTP and 1 mM NSAAH at 4° C. for 30 minutes. The drop consisting of hRRM1-TTP-NSAAH was cross-seeded with preformed hRRM1-dTTP crystals previously reported in reference to form the co-crystal of hRRM1-TTP-NSAAH. The crystals were screened by the hanging drop method. The well solution for crystallization was composed of 100 mM Tris, pH 7.9, 200 mM Li$_2$SO$_4$, and 19% PEG-3350. Diffraction quality crystals appeared after one week and which was transferred to the mother liquor, with 20% glycerol as cryo-protectant, and then flash frozen in liquid nitrogen for data collection. Diffraction data were collected with crystals flash cooled at 100K in a stream of liquid $N_2$ using a synchrotron radiation source, NECAT beamline, at APS (Advanced Photon Source) Chicago. The crystals were of space group P2$_1$2$_1$2$_1$ and diffracted to 2.66 Å resolution.

Structure Solution and Refinement

The structure of the NSAAH-hRRM1 complex structure was solved by molecular replacement using a previously solved structure of hRRM1-GDP-dTTP (PDB ID 3HNC) as a search model. Molecular replacement gave a single prominent solution after rotation and translation function. The initial solution was refined by rigid body refinement, which produced a clearly interpretable electron density map for the overall structure. The ligand density for NSAAH was clearly observed at the active site of hRRM1. Manual adjustment of the backbone and sidechain of the model was conducted in Coot. Crystallographic refinement was carried out using the programs Phenix and refmac 5 within CCP4 suite. Difference Fourier maps with coefficients 2|F$_o$|−|F$_c$| and |F$_o$|−|F$_c$| were used to model NSAAH interacting with amino acid residues at the catalytic site. After a few rounds of model building water molecules were added using the |F$_o$|−|F$_c$| map peaks above 3.0 σ. The value of R$_{free}$ can be used as an indicator to validate the water picking and refinement and to avoid any possible over fitting of the data.

Cell-Free Inhibition Studies

The IC$_{50}$ was determined using the method described in reference. Briefly, boronate chromatography was used to separate the product. Six concentrations of NSAAH were studied ranging from 5-100 μM. The assay was repeated in triplicate. Data were fitted in GraphPad Prism 6.05 using a sigmoidal dose-response curve.

Binding Studies Using Fluorescence Quenching

As described, to assay binding NSAAH was titrated into a solution of 0.5 mg hRRM1 at 10-200 μM in 10 μM increments. The emission spectrum was recorded over 300-400 nm using a Jobin Yvon-Spex fluorescence spectrophotometer. The data were fitted by nonlinear regression using the one-site binding (hyperbola) equation Y=Bmax*X/(Kd (app)+X), where Bmax is the maximum extent of quenching and Kd(app) is the apparent dissociation constant, using GraphPad Prism 6.05. Measurements were recorded in duplicate.

Blood Progenitor Colony Forming Unit (CFU) Assay

The CFU assay was performed in the Hematopoietic Biorepository and Cellular Therapy Core Facility of the Case Comprehensive Cancer Center using a standardized protocol.

Briefly, mobilized peripheral blood mononuclear cells were collected from healthy donors by apheresis after Neupogen stimulation under University Hospitals IRB Protocol #09-90-195. Excess discarded cells were diluted to $1(10^6)$ cells/mL in RPMI1640+15% fetal bovine serum, 100 U/mL penicillin, 100 µg/mL streptomycin and 50.4 units/ml GM-CSF. Drug solution was added to the cell suspension and 9× volume of complete methylcellulose (Methocult H4434+50 µM hemin.). The methylcellulose/cell suspension was aliquoted into triplicate 35-mm gridded tissue culture plates and incubated in a humidified 5% $CO_2$ incubator at 37° C. for 14 days. Plates were counted visually and clusters of >50 cells were scored as surviving colonies.

Cancer Cell Line Growth Inhibition Assay

The growth inhibition assay was performed in the Preclinical Drug Testing Laboratory of the Case Comprehensive Cancer Center using a standardized protocol. Cell lines (human colon cancer HCT116 and human pancreas ductal adenocarcinoma Panc cells) were maintained in standard growth media; RPMI1640+10% FBS+2 mM glutamine+100 U/ml penicillin, 100 ug/ml streptomycin and shown to be negative for *mycoplasma* contamination using the MycoAlert™ *Mycoplasma* Detection kit (Lonza, Basel, Switzerland). Cell identity was verified by by Short Tandem Repeat (STR) testing performed using the Promega StemElite kit, in the Genetic Resources Core Facility (GRCF) at Johns Hopkins University.

For growth inhibition assays, cells were harvested by trypsinization and seeded into 96-well tissue culture plates at 2500 cells/mL. The following day an equal volume of 2×-drug containing medium was added to each well. The cells were cultured for 3 additional days at 37° C. in a 5% $CO_2$ humidified incubator. Cell growth was assessed by measuring DNA content per well using the method of Labarca and Paigen. Dye fluorescence was measured in a Perkin-Elmer 1420 Victor 3 Multilabel plate reader using 355 nm excitation and 460 nm emission.

Example 2

NSAAH Acts Synergistically with Oxidiazole OXO F

We further illustrate that NSAAH, the previously described original hydrozone lead compound can act synergistically with a newly identified oxidiazole compound OxaF.

As shown in Table 3 (below), the "r" values represents how well the data fits the curves generated by Calcusyn, the closer to 1.00 the better.

The CIs were generated with a 1:1 ratio of NSAAH to OxaF and indicates evidence of a syngergistic effect using a combination of the two RRmods in HCT-116 and Pacn1 cancer cell line growth inhibition assays described above.

TABLE 3

|  | HCT-116 | | Panc1 | |
| --- | --- | --- | --- | --- |
|  | Dm (uM) | r | Dm (um) | r |
| Oct. 21, 2016 | | | | |
| NSAAH (old) | 0.166 | 0.914 | .48 | .940 |
| NSAAT E | 66.8 | 0.719 | >10 | 0.350 |

TABLE 3-continued

|  | HCT-116 | | Panc1 | |
| --- | --- | --- | --- | --- |
|  | Dm (uM) | r | Dm (um) | r |
| NSAAT F | >10 | .0835 | >10 | 0.237 |
| Oxa A | 6.89 | 0.767 | 53.58 | 0.849 |
| Oxa F | 1.41 | 0.944 | 1.92 | 0.964 |
| Oxa N | 23.91 | 0.832 | >10 | 0.809 |
| Oct. 24, 2016 | | | | |
| NSAAH (old) | 0.234 | 0.905 | 0.55 | 0.900 |
| NSAAH (new) | 0.176 | 0.902 | 0.85 | 0.889 |
| 373955 | >10 | 0.526 | >10 | 0.196 |
| 186064 | 255 | 0.632 | >10 | 0.111 |
| 374101 | >10 | 0.324 | >10 | 0.288 |
| 481887 | >10 | 0.481 | >10 | 0.041 |
| 5000059 | >10 | 0.044 | >10 | 0.137 |
| Oct. 24, 2016 | | | | |
| NSAAH (old) + Oxa F CI | 0.157 | 0.900 | 0.344 | 0.940 |
| ED50 | 0.782 | | 0.806 | |
| ED75 | 0.878 | | 0.810 | |
| ED90 | 0.993 | | 0.816 | |

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

The invention claimed is:

1. A method of modulating ribonucleotide reductase activity in a neoplastic cell comprising administering to the cell an amount of a ribonucleotide reductase allosteric modulator (RRmod), the RRmod comprising an oxadiazole that is administered at an amount effective to inhibit neoplastic cell growth, wherein the RRmod is an oxadiazole having the following formula (IV):

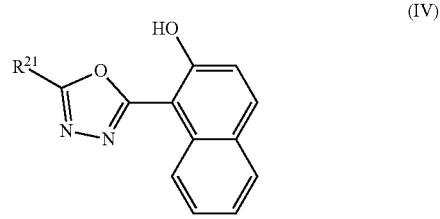

or pharmaceutically acceptable salts thereof:

wherein $R^{21}$ is selected from the group consisting of:

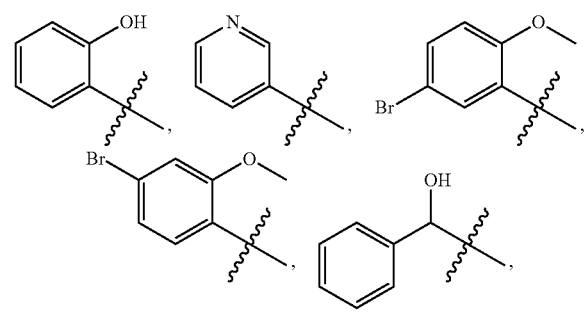

-continued

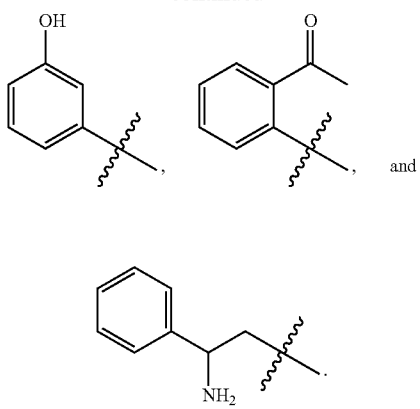, and

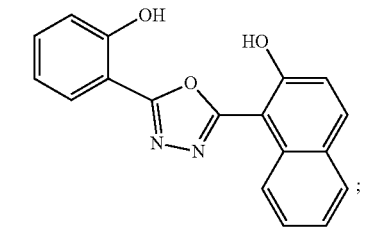

2. The method of claim 1, wherein the RRmod is selected from the group consisting of:

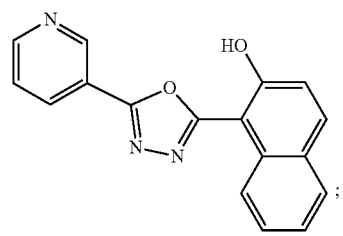

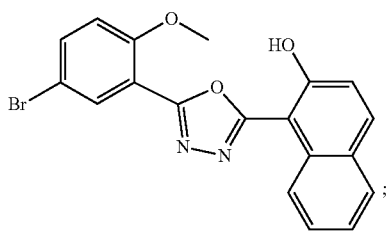

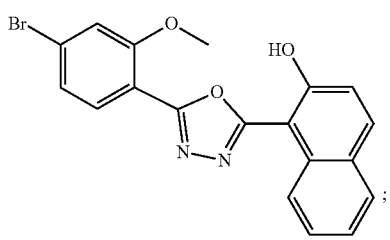

-continued

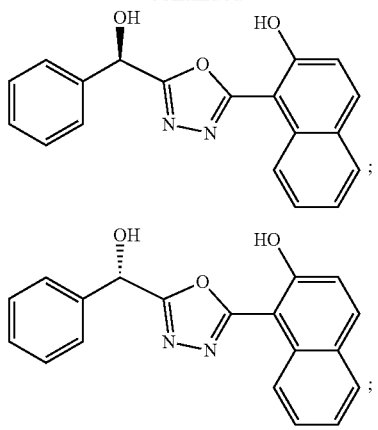

and
pharmaceutically acceptable salts thereof.

3. The method of claim 1, the cell comprising a cancer cell.

4. The method of claim 3, the cancer cell comprising a pancreatic, breast, lung, colon or glioblastoma cancer cell.

5. A method of treating a neoplastic disorder in a subject comprising:
administering to neoplastic cells of the subject a therapeutically effective amount of a pharmaceutical composition, the composition comprising a reductase allosteric modulator (RRmod), the RRmod including an oxadiazole that is administered at an amount effective to inhibit neoplastic cell growth, wherein the RRmod is an oxadiazole having the following formula (IV):

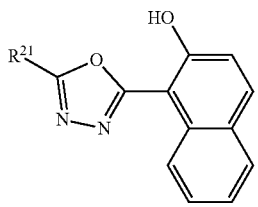

(IV)

or pharmaceutically acceptable salts thereof:

wherein $R^{21}$ is selected from the group consisting of:

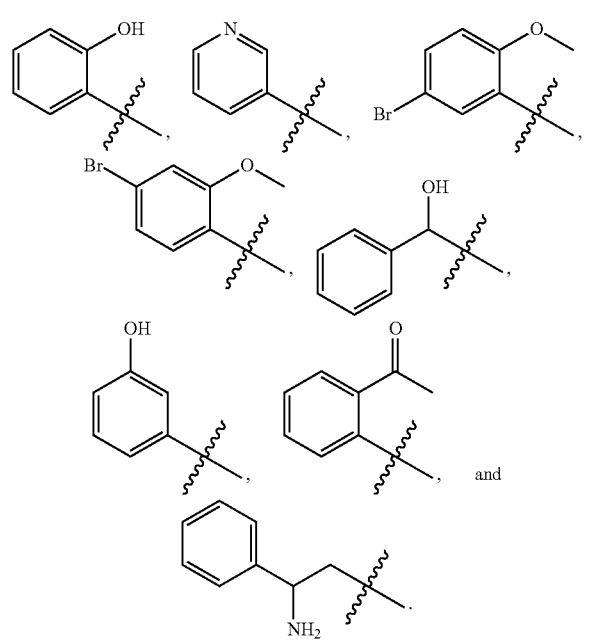

6. The method of claim 5, wherein the RRmod is selected from the group consisting of:

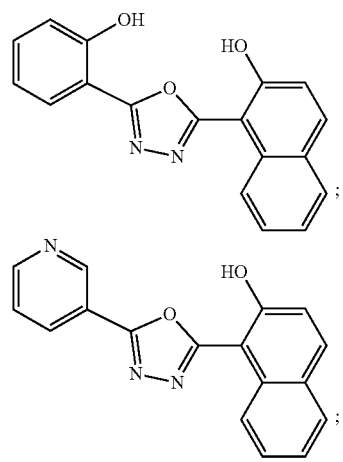

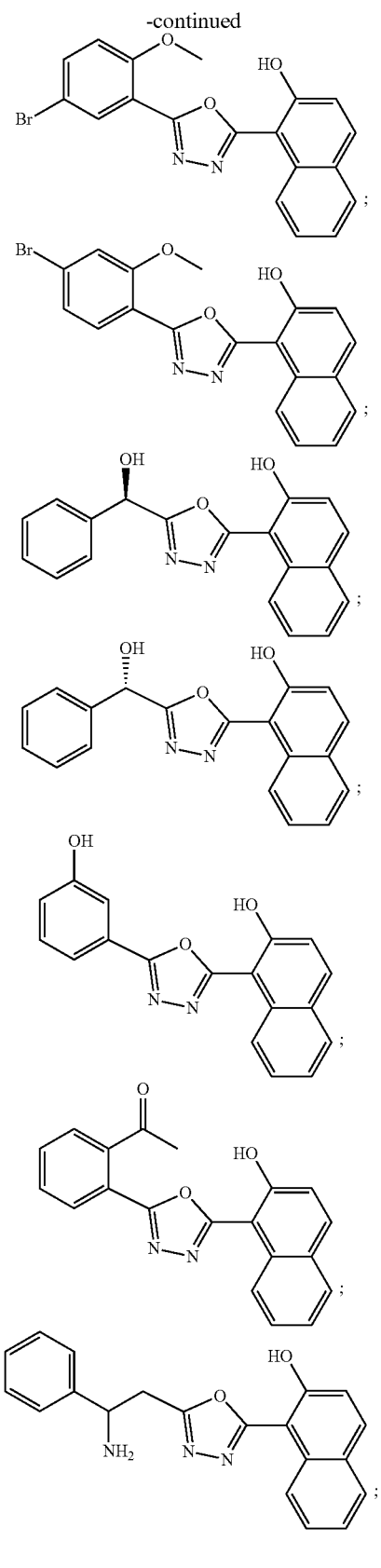

and
pharmaceutically acceptable salts thereof.

7. The method of claim 5, the neoplastic disorder comprising cancer.

8. The method of claim 7, wherein the cancer includes pancreatic, breast, lung, colon or glioblastoma cancer.

9. The method of claim 5, further administering another therapeutic agent in conjunction with the RRmod.

10. The method of claim 9, the other therapeutic agent comprising at least one of a chemotherapeutic agent, an antimetabolite, a DNA damaging agent, a ribonucleotide reductase inhibiting agent, an antitumorgenic agent, an antimitotic agent, an antiviral agent, an antineoplastic agent, an immunotherapeutic agent, and a radiotherapeutic agent.

11. The method of claim 1, wherein the RRmod has a cellular cytotoxicity 1050 of 10 μm against HCT-116 and PANC-1 cancer cell lines.

12. The method of claim 5, wherein the RRmod has a cellular cytotoxicity 1050 of 10 μm against HCT-116 and PANC-1 cancer cell lines.

* * * * *